(12) United States Patent
Hershberger et al.

(10) Patent No.: US 11,534,181 B2
(45) Date of Patent: Dec. 27, 2022

(54) SURGICAL SYSTEMS WITH TWIST-LOCK BATTERY CONNECTION

(71) Applicant: Stryker Corporation, Kalamazoo, MI (US)

(72) Inventors: David E. Hershberger, Kalamazoo, MI (US); Eric K. Diehl, San Francisco, CA (US); Steven Brown, Austin, TX (US); Heather Benoit, Austin, TX (US)

(73) Assignee: Stryker Corporation, Kalamazoo, MI (US)

( * ) Notice: Subject to any disclaimer, the term of this patent is extended or adjusted under 35 U.S.C. 154(b) by 453 days.

(21) Appl. No.: 16/619,979

(22) PCT Filed: Jun. 7, 2018

(86) PCT No.: PCT/US2018/036444
§ 371 (c)(1),
(2) Date: Dec. 6, 2019

(87) PCT Pub. No.: WO2018/226945
PCT Pub. Date: Dec. 13, 2018

(65) Prior Publication Data
US 2020/0197027 A1    Jun. 25, 2020

Related U.S. Application Data

(60) Provisional application No. 62/517,331, filed on Jun. 9, 2017.

(51) Int. Cl.
*A61B 17/00*        (2006.01)
*A61B 17/16*        (2006.01)
(Continued)

(52) U.S. Cl.
CPC ........ *A61B 17/1622* (2013.01); *A61B 17/068* (2013.01); *A61B 17/14* (2013.01);
(Continued)

(58) Field of Classification Search
CPC ........... A61B 2017/00477; A61B 2017/00734; H01M 2010/4278; H01M 2220/30; H01M 50/213; H01M 50/502
(Continued)

(56) References Cited

U.S. PATENT DOCUMENTS 6,018,227 A    1/2000 Kumar et al.
6,553,642 B2   4/2003 Driessen
(Continued)

FOREIGN PATENT DOCUMENTS

CN    105358085 A    2/2016
EP      2338644 A2    6/2011
(Continued)

OTHER PUBLICATIONS

International Search Report for Application No. PCT/US2018/036444 dated Nov. 12, 2018, 4 pages.
(Continued)

*Primary Examiner* — Nathan J Jenness
(74) *Attorney, Agent, or Firm* — Howard & Howard Attorneys PLLC

(57) ABSTRACT

A surgical system comprises a handpiece and a battery. The handpiece includes a body, a handpiece controller, and a handpiece connector with a first coupler, a handpiece voltage terminal, and a handpiece data terminal. The battery has a housing, a cell, a battery controller, and a battery connector with a second coupler to rotatably engage the first coupler, a battery voltage terminal, and a battery data terminal. The second coupler receives the first coupler at an initial radial position and permits rotation to a first secured radial position and a second secured radial position. Rotation from the initial radial position to the first secured radial position engages the voltage terminals to transmit power between the cell and the handpiece controller, and rotation to the second
(Continued)

secured radial position engages the data terminals to communicate data between the controllers while maintaining engagement between the voltage terminals.

34 Claims, 27 Drawing Sheets

(51) Int. Cl.
  *A61B 17/068* (2006.01)
  *A61B 17/14* (2006.01)
(52) U.S. Cl.
  CPC .............. *A61B 2017/00017* (2013.01); *A61B 2017/0046* (2013.01); *A61B 2017/00367* (2013.01); *A61B 2017/00477* (2013.01); *A61B 2017/00734* (2013.01)
(58) Field of Classification Search
  USPC ................................................. 320/112, 114
  See application file for complete search history.

(56) References Cited

U.S. PATENT DOCUMENTS

| | | |
|---|---|---|
| 6,840,335 B1 | 1/2005 | Wu |
| 6,887,244 B1 | 5/2005 | Walker et al. |
| 7,121,362 B2 | 10/2006 | Hsu et al. |
| 7,186,117 B2 | 3/2007 | Chen |
| 7,205,745 B2 | 4/2007 | Murashige et al. |
| 7,429,430 B2 | 9/2008 | Mooty et al. |
| 7,619,387 B2 | 11/2009 | Amend et al. |
| 7,705,559 B2 | 4/2010 | Powell et al. |
| 8,822,067 B2 | 9/2014 | Johnson et al. |
| 8,878,490 B2 | 11/2014 | LaSota et al. |
| 8,974,932 B2 | 3/2015 | McGahan et al. |
| 9,419,462 B2 | 8/2016 | Sollanek |
| 9,461,281 B2 | 10/2016 | Wackwitz et al. |
| 9,496,729 B2 | 11/2016 | Woods |
| 9,606,188 B2 | 3/2017 | Noda et al. |
| 9,819,051 B2 | 11/2017 | Johnson et al. |
| 9,872,696 B2 | 1/2018 | Smith et al. |
| 9,884,416 B2 | 2/2018 | Chellew et al. |
| 10,224,566 B2 | 3/2019 | Johnson et al. |
| 10,276,844 B2 | 4/2019 | Wackwitz et al. |
| 10,511,008 B2 | 12/2019 | Brush et al. |
| 2006/0267548 A1* | 11/2006 | Uehlein-Proctor ....... B25F 5/02 320/107 |
| 2007/0090788 A1 | 4/2007 | Hansford et al. |
| 2007/0257638 A1* | 11/2007 | Amend ............... H01M 50/296 320/112 |
| 2010/0004669 A1 | 1/2010 | Smith et al. |
| 2012/0071796 A1* | 3/2012 | Smith ............ A61B 17/320092 601/3 |
| 2018/0205051 A1 | 7/2018 | Sakai et al. |
| 2019/0027720 A1 | 1/2019 | Rejman et al. |
| 2019/0290297 A1 | 9/2019 | Haider et al. |

FOREIGN PATENT DOCUMENTS

| | | |
|---|---|---|
| JP | 2009205980 A | 9/2009 |
| JP | 2013239259 A | 11/2013 |
| JP | 2014020798 A | 2/2014 |
| JP | 2015507455 A | 3/2015 |
| WO | 2007050439 A2 | 5/2007 |
| WO | 2007090025 A1 | 8/2007 |
| WO | 2019153349 A1 | 8/2019 |

OTHER PUBLICATIONS

Synthes, "Power Drive Photograph, View No. 1", May 24, 2018, 1 page.
Synthes, "Power Drive Photograph, View No. 2", May 24, 2018, 1 page.
Synthes, "Power Drive Photograph, View No. 3", May 24, 2018, 1 page.
Synthes, "Power Drive Photograph, View No. 4", May 24, 2018, 1 page.
Synthes, "Power Drive Photograph, View No. 5", May 24, 2018, 1 page.
Synthes, "Power Drive User's Manual", 2000, pp. 1-29.
English language abstract for CN 105358085 A extracted from espacenet.com database on Mar. 14, 2022, 2 pages.
English language abstract and machine-assisted English translation for JP 2009-205980 A extracted from espacenet.com database on Apr. 27, 2022, 25 pages.
English language abstract and machine-assisted English translation for JP 2013-239259 A extracted from espacenet.com database on Apr. 27, 2022, 15 pages.
English language abstract for JP 2014-020798 A extracted from espacenet.com database on Apr. 27, 2022, 2 pages.
English language abstract for JP 2015-507455 A extracted from espacenet.com database on Apr. 27, 2022, 2 pages.

\* cited by examiner

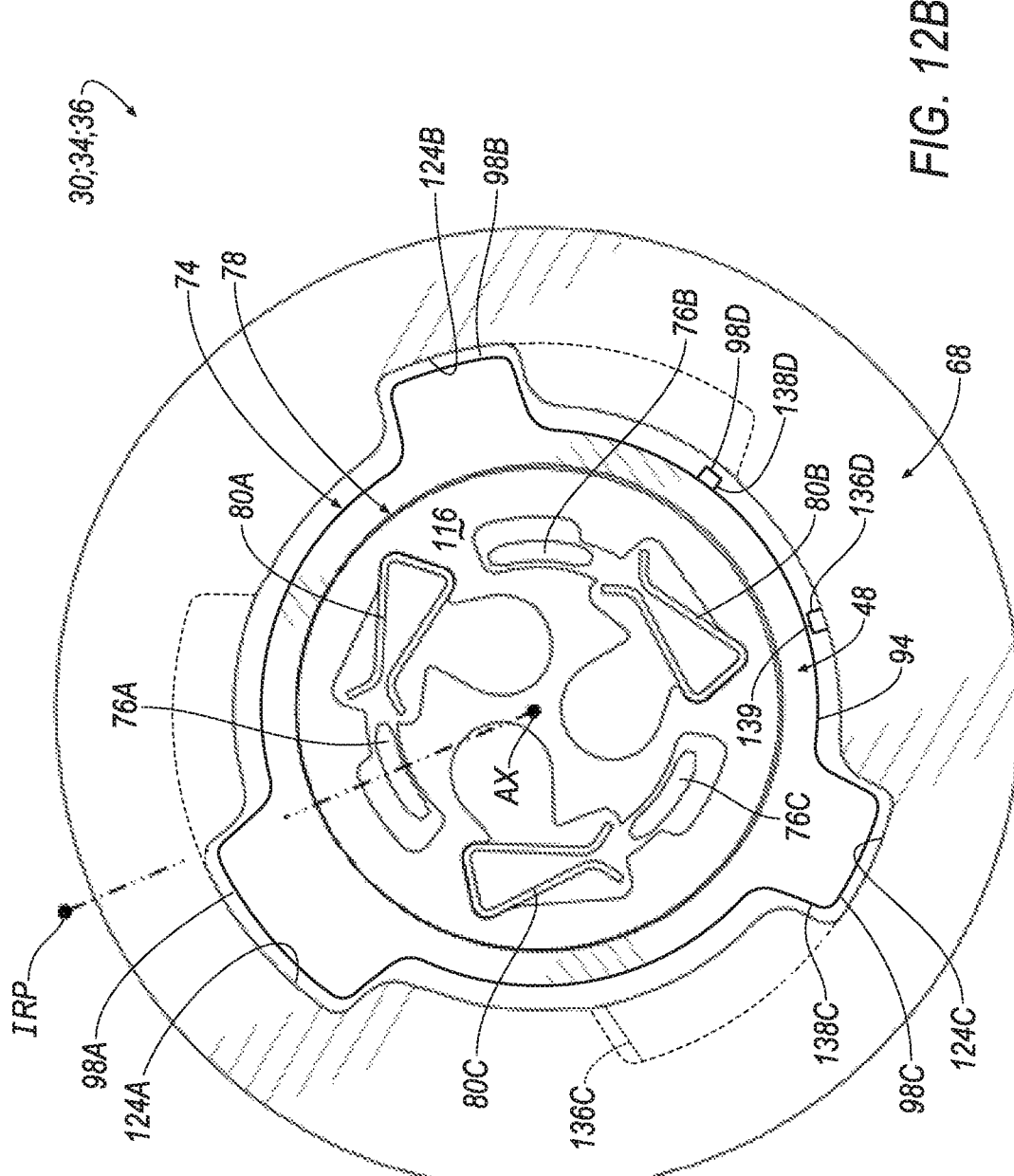

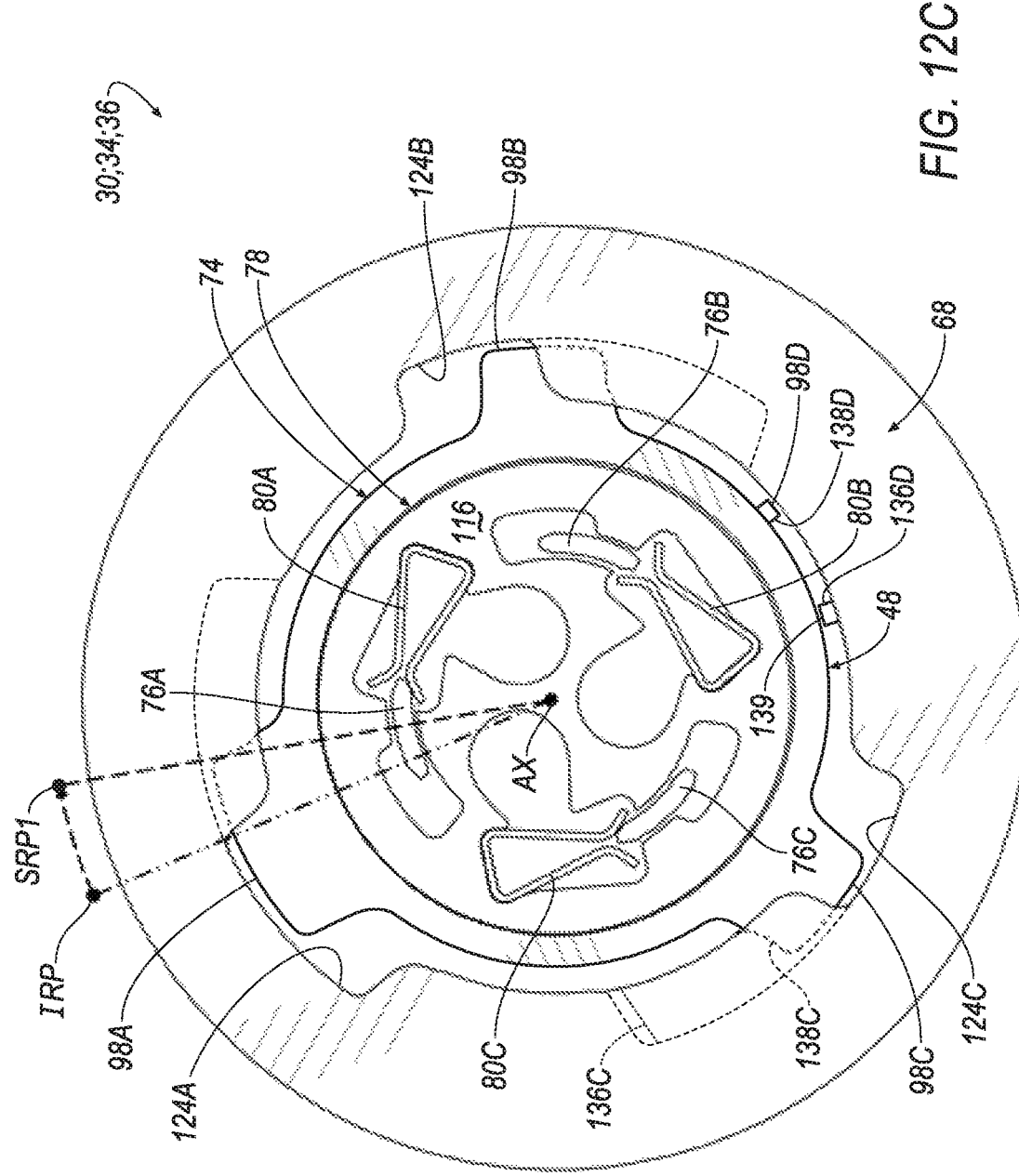

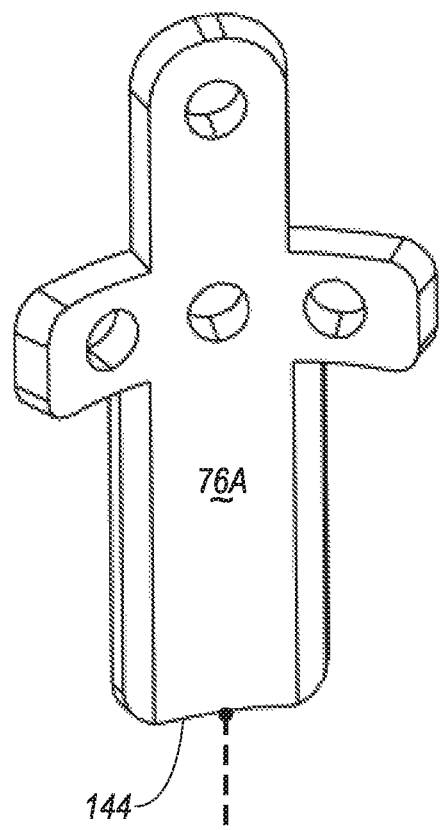
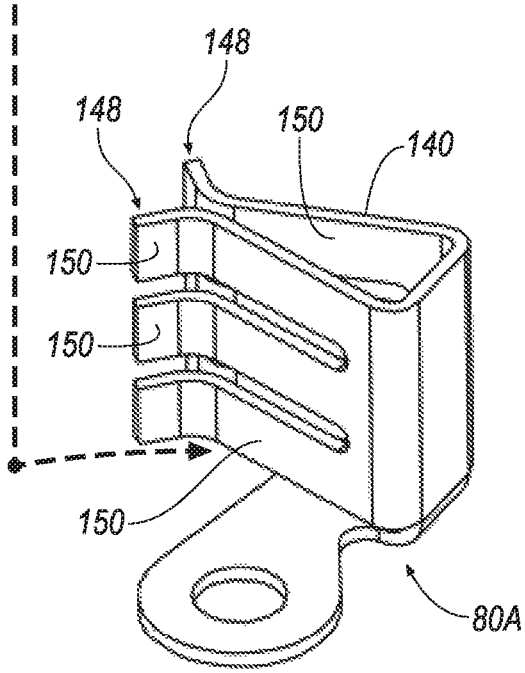
FIG. 14A

SURGICAL SYSTEMS WITH TWIST-LOCK BATTERY CONNECTION

CROSS-REFERENCE TO RELATED APPLICATIONS

This patent application claims priority to and all advantages of International Patent Application No. PCT/US2018/036444, filed Jun. 7, 2018 which claims priority to and all the benefits and advantages of U.S. Provisional Patent Application No. 62/517,331 filed on Jun. 9, 2017, both of which are herein incorporated by reference in their entireties.

BACKGROUND

Conventional medical and surgical procedures routinely involve the use of battery-powered surgical systems, such as drills, sagittal saws, and other tools, which allow surgeons to approach and manipulate surgical sites where tethered connections to power supplies, consoles, and the like are undesirable. Surgical tools of this type are generally configured to releasably attach to a rechargeable battery pack, which provides a source of power to the tool until its charge is depleted. Both the tool and the battery pack are typically designed to be used multiple times, and are manufactured in a way that allows them to be cleaned and sterilized between uses.

It will be appreciated that the charge in a single battery pack may be insufficient for certain procedures, such as those involving extensive drilling or cutting with the tool. In such circumstances, when the charge in one battery pack has been depleted, the surgeon will remove the depleted battery pack from the tool and subsequently attach a different, charged battery pack to the tool before continuing the procedure. The depleted battery pack can then be cleaned, sterilized, re-charged, and subsequently re-used in another procedure.

While conventional battery-powered surgical systems have generally performed well for their intended use, the process of removing the battery pack from the tool can be difficult, in particular because the tool and the battery pack are often designed to seal or otherwise tightly engage against each other to prevent inadvertent disconnection or damage to electrical contacts during use, reduce vibration and noise, and help discourage the ingress of contaminants between the tool and the battery pack. Because of this, removal of the battery pack sometimes results in damage to portions of the tool or battery pack which, in turn, may result in safety and/or handling concerns. Accordingly, there remains a need in the art for addressing one or more of these deficiencies.

BRIEF DESCRIPTION OF THE DRAWINGS

Advantages of the examples disclosed herein will be readily appreciated as the same becomes better understood after reading the subsequent description taken in connection with the accompanying drawings.

FIG. 12B is a schematic representation depicting engagement of the battery connector and the handpiece connector at the initial radial position shown in FIG. 11C.

FIG. 12C is another schematic representation depicting engagement of the battery connector and the handpiece connector of FIG. 12B, shown with the handpiece connector rotated from the initial radial position to one secured radial position relative to the battery connector.

FIG. 14A is a perspective view showing a handpiece terminal of the handpiece connector of FIG. 8 spaced from a battery terminal of the battery connector of FIG. 4.

DETAILED DESCRIPTION

Figure 1:
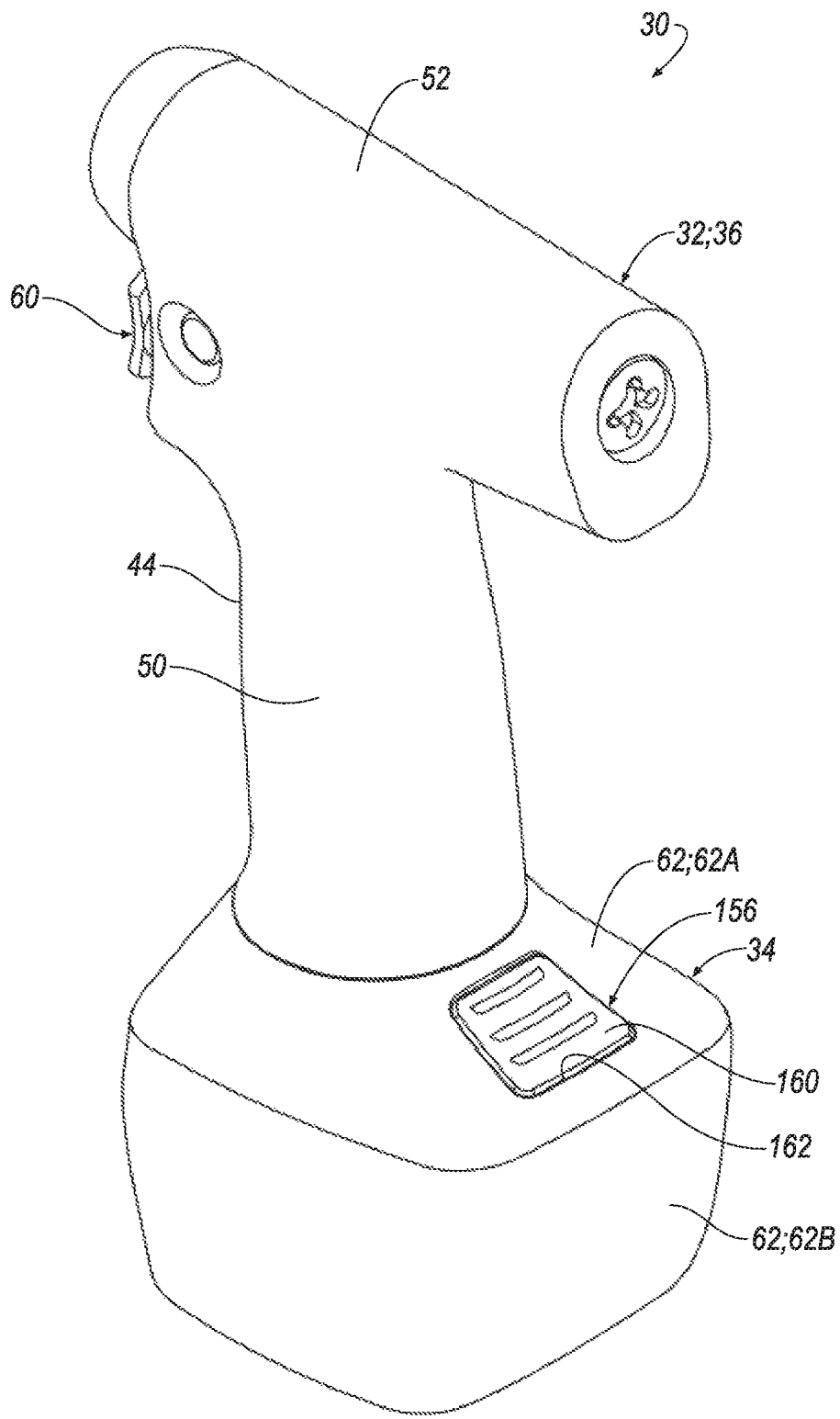
FIG. 1 is a perspective view of a system comprising a handpiece connected to a battery according to one example.

With reference to the drawings, like numerals are used to designate like structure throughout the several views.

The word "receive" and its variants (e.g., received, receives), as used herein, describe mechanical relationships between components and include relationships in which one component fits at least in part within another component, independent of which component fits inside which component, i.e., a male component may receive a female component, and a female component may receive a male component. The term "radial position" and its variants (e.g., radially spaced), as used herein, mean a position depending on a relative rotative orientation of a component relative to an established reference point, e.g., a second component, with the radial position being alternatively characterizable as a circumferential position or an angular position.

A surgical system comprises a hand piece and an autoclavable battery. The handpiece comprises a body, a handpiece controller, and a handpiece connector. The handpiece connector is operatively coupled to the body and comprises a handpiece voltage terminal and a handpiece data terminal with each connected to the handpiece controller and a first coupler. The autoclavable battery comprises a housing, a rechargeable cell for storing an electric charge, a battery controller, and a battery connector operatively coupled to the housing. The battery connector comprises a battery voltage terminal and a battery data terminal with each connected to the battery controller, and a second coupler for rotatably engaging the first coupler. The second coupler is further configured to receive the first coupler along an axis at an initial radial position. The second coupler is also configured to, in the initial radial position, permit relative axial movement between the battery and the handpiece. The relative axial movement permits rotation of the battery relative to the handpiece from the initial radial position to a first secured radial position and to a second secured radial position where relative axial movement between the battery and the handpiece is constrained. The handpiece terminals and the battery terminals are arranged such that rotation from the initial radial position to the first secured radial position brings the handpiece voltage terminal into engagement with the battery voltage terminal to transmit power between the cell and the handpiece controller. Rotation from the first secured radial position to the second secured radial position brings the handpiece data terminal into engagement with the battery data terminal to communicate data between the battery controller and the handpiece controller while maintaining engagement between the handpiece voltage terminal and the battery voltage terminal.

A surgical system comprises a hand piece and an autoclavable battery. The handpiece is for performing a surgical procedure. The handpiece comprises a body, a handpiece controller for operating the handpiece, and a handpiece connector. The handpiece connector is operatively coupled to the body and comprises a first coupler, a handpiece power terminal, and a handpiece data terminal. The autoclavable battery is for providing a source of electrical power to the handpiece. The battery comprises a housing, a cell for storing an electric charge, a battery controller, and a battery connector operatively coupled to the housing. The battery additionally comprises a second coupler for rotatably engaging the first coupler, a battery power terminal, and a battery data terminal. The second coupler is further configured to receive the first coupler of the handpiece connector at an initial radial position. The second coupler is also configured to, in the initial radial position, permit relative axial movement between the battery and the handpiece. The relative axial movement permits rotation of the battery relative to the handpiece from the initial radial position to a first secured radial position and to a second secured radial position where relative axial movement between the battery and the handpiece is constrained. The handpiece terminals and the battery terminals are arranged such that rotation from the initial radial position to the first secured radial position brings the handpiece power terminal into engagement with the battery power terminal to transmit power between the cell and the handpiece controller. Rotation from the first secured radial position to the second secured radial position brings the handpiece data terminal into engagement with the battery data terminal to communicate data between the battery controller and the handpiece controller while maintaining engagement between the handpiece power terminal and the battery power terminal.

The surgical system may further have the handpiece power terminal and the handpiece data terminal radially spaced from each other about the axis at a handpiece terminal arc length. The battery power terminal and the battery data terminal may be radially spaced from each other about the axis at a battery terminal arc length different from the handpiece terminal arc length.

The surgical system may further comprise a charger for storing an electrical charge in the cell.

A surgical system comprises a module and an autoclavable battery. The module comprises a body, a module controller, and a module connector. The module connector is operatively coupled to the body and comprises a first coupler, a first module terminal, a second module terminal, and a third module terminal. The autoclavable battery comprises a housing, a cell for storing an electric charge, a battery controller, and a battery connector. The battery connector is operatively coupled to the housing. The battery connector comprises a second coupler for rotatably engaging the first coupler, a first battery terminal, a second battery terminal, and a third battery terminal. The second coupler is further configured to receive the first coupler of the module connector at an initial radial position where relative axial movement between the battery and the module is permitted. The second coupler is configured to permit rotation of the battery relative to the module from the initial radial position to a first secured radial position and to a second secured radial position where relative axial movement between the battery and the module is constrained. The module terminals and the battery terminals are arranged such that rotation from the initial radial position to the first secured radial position brings the first module terminal into engagement with the first battery terminal. The module terminals and the battery terminals are also arranged such that rotation from the first secured radial position to the second secured radial position brings the second module terminal into engagement with the second battery terminal while maintaining engagement between the first module terminal and the first battery terminal.

A surgical system comprises a module and an autoclavable battery. The module comprises a body, a module controller, and a module connector operatively coupled to the body. The module connector comprises a first coupler, a first module terminal, a second module terminal, and a third module terminal. The autoclavable battery comprises a housing, a cell for storing an electric charge, a battery controller, and a battery connector. The battery connector is operatively coupled to the housing. The battery connector comprises a second coupler to rotatably engage the first coupler, a first battery terminal, a second battery terminal, and a third battery terminal. The second coupler is further configured to receive the first coupler of the module connector at an initial radial position where relative axial movement between the battery and the module is permitted. The second coupler is also configured to permit rotation of the battery relative to the module from the initial radial position to a first secured radial position and to a second secured radial position where relative axial movement between the battery and the module is constrained. The module terminals and the battery terminals are arranged such that rotation from the initial radial position to the first secured radial position brings the first module terminal into engagement with the first battery terminal and brings the third module terminal into engagement with the third battery terminal, and rotation from the first secured radial position to the second secured radial position brings the second module terminal into engagement with the second battery terminal while maintaining engagement between the first module terminal and the first battery terminal and between the third module terminal and the third battery terminal.

The module may be further defined as a handpiece for performing a surgical procedure.

The module may alternatively be further defined as a charger for storing an electrical charge in the cell.

A surgical system comprises a handpiece and a battery. The handpiece is for performing a surgical procedure. The handpiece comprises a body, a handpiece controller for operating the handpiece, and a handpiece connector operatively coupled to the body. The body comprises a first coupler, a handpiece power terminal, and a handpiece data terminal. The battery is for providing a source of electrical power to the handpiece. The battery comprises a housing, a cell for storing an electric charge, a battery controller, and a battery connector. The battery connector is operatively coupled to the battery housing and comprises a second coupler to rotatably engage the first coupler, a battery power terminal, and a battery data terminal. The second coupler of the battery connector is further configured to receive the first coupler of the handpiece connector along an axis. The handpiece power terminal and the handpiece data terminal are radially spaced from each other about the axis at a handpiece terminal arc length. The battery power terminal and the battery data terminal are radially spaced from each other about the axis at a battery terminal arc length different from the handpiece terminal arc length.

The handpiece connector may further comprise a tab extending outwardly from the first coupler. The battery connector may further comprise a slot formed adjacent to the second coupler to receive the tab of the handpiece connector at the initial radial position, permitting rotation of the battery relative to the handpiece between the initial radial position and the first and second secured radial positions.

The slot of the battery connector may comprise an axial portion to receive the tab of the handpiece connector at the initial radial position, and a radial portion adjacent to the axial portion to receive the tab in the plurality of secured radial positions.

The radial portion of the slot of the battery connector may define a slot securing surface. The tab of the handpiece connector may define a tab securing surface arranged to abut the slot securing surface when the tab is disposed in the radial portion of the slot.

The tab of the handpiece connector may comprise a transition chamfer shaped to facilitate movement from the initial radial position toward the first and second secured radial positions.

The handpiece connector may further comprise a first tab extending outwardly from the first coupler and a second tab spaced from the first tab extending outwardly from the first coupler. The battery connector may further comprise a first slot formed adjacent to the second coupler to receive the first tab of the handpiece connector at the initial radial position and a second slot formed adjacent to the second coupler and spaced from the first slot to receive the second tab of the handpiece connector at the initial radial position.

The second slot of the battery connector may be shaped differently from the first slot to prevent the first tab of the handpiece connector from being received within the second slot.

The second slot of the battery connector may be smaller than the first slot to prevent the first tab of the handpiece connector from being received within the second slot.

The first coupler of the handpiece connector may be further configured to be received by the second coupler of the battery connector along an axis. The first and second tabs of the handpiece connector may be radially spaced from each other about the axis to prevent the first tab of the handpiece connector from being received within the second slot of the battery connector.

The first coupler of the handpiece connector may comprise an outer first coupler surface and an inner first coupler surface extending to a first coupler end.

The second coupler of the battery connector may comprise a second coupler member and a second coupler channel. The second coupler member may define a second coupler member surface shaped to engage the inner first coupler surface of the handpiece connector. The second coupler channel may be formed adjacent to the second coupler member and may define an inner channel surface shaped to engage the outer first coupler surface of the handpiece connector.

The second coupler member of the battery connector may extend to a second coupler end. A first receptacle may be formed in the second coupler end to accommodate the battery power terminal. A second receptacle may be formed in the second coupler end to accommodate the battery data terminal.

The battery terminals may each extend towards the second coupler end to respective battery terminal ends.

The battery terminal ends may be spaced from the second coupler end.

A battery terminal gap may be defined between the battery terminal ends and the second coupler end.

The inner first coupler surface of the handpiece connector may define a socket portion. The handpiece terminals may be disposed in the socket portion.

The handpiece terminals may each extend towards the first coupler end to respective handpiece terminal ends.

The handpiece terminal ends may be spaced from the first coupler end, and may define a handpiece terminal gap therebetween.

A handpiece terminal gap may be defined between the handpiece terminal ends and the first coupler end.

The handpiece terminals may each have a generally arc-shaped-rectangular profile.

The battery terminals may each comprise a pair of arms arranged to receive one of the handpiece terminals therebetween.

The arms of each of the battery terminals may be resiliently biased towards each other.

The arms of each of the battery terminals may comprise a plurality of fingers each arranged to engage one of the handpiece terminals.

The couplers may be configured such that predetermined rotation about the axis from an initial radial position to a secured radial position restricts relative axial movement between the battery and the handpiece.

The handpiece connector may further comprise a handpiece ground terminal, and the battery connector may further comprise a battery ground terminal. The handpiece ground terminal and the battery ground terminal may be arranged such that rotation from the initial radial position to the first secured radial position brings the handpiece ground terminal into engagement with the battery ground terminal to ground the handpiece controller and the cell.

The handpiece connector may further comprise a second handpiece voltage terminal. The battery connector may further comprise a second battery voltage terminal. The second handpiece voltage terminal and the second battery voltage terminal may be arranged such that rotation from the initial radial position to the first secured radial position brings the second handpiece voltage terminal into engagement with the second battery voltage terminal.

The handpiece connector may further comprise a catch arranged adjacent to the first coupler. The battery may further comprise a release mechanism supported in the housing, defining a latch shaped to engage the catch in one of the secured radial positions to restrict rotation from the secured radial position.

The first coupler of the handpiece connector may be shaped to engage against the latch of the release mechanism at the initial radial position to compress the release bias element until rotation from the initial radial position toward one of the secured radial positions brings the latch and the catch into engagement.

The battery may further comprise a release bias element interposed between the housing and the release mechanism arranged to urge the latch into engagement with the catch.

A method of using a surgical system comprises providing a handpiece, providing an autoclavable battery, positioning the battery connector, moving the battery connector and rotating the battery. The handpiece comprises a handpiece connector, the handpiece connector defining an axis. The autoclavable battery comprises a battery connector configured for releasable attachment to the handpiece connector. The battery connector is positioned along the axis. The battery connector is moved into axial engagement with the handpiece connector at an initial radial position. The battery is rotated about the axis, relative to the handpiece, from the initial radial position to a secured radial position to secure the battery to the handpiece.

A method of using a surgical system comprises providing a handpiece, providing an autoclavable battery, positioning the battery connector, moving the battery connector and rotating the battery. The handpiece comprises a handpiece connector, the handpiece connector including a handpiece voltage terminal and a handpiece data terminal. The handpiece connector also defines an axis. The autoclavable battery comprises a battery connector including a battery voltage terminal and a battery data terminal. The battery connector is configured for releasable attachment to the handpiece connector. The battery connector is positioned along the axis. The battery connector is moved into axial engagement with the handpiece connector at an initial radial position. The battery is rotated relative to the handpiece about the axis from the initial radial position to a first secured radial position, engaging the battery voltage terminal with the handpiece voltage terminal. The battery is rotated to a second secured radial position, engaging the battery data terminal with the handpiece data terminal. The second secured radial position is greater than the first secured radial position. The battery is rotated to a final secured radial position greater than the second secured radial position to secure the battery to the handpiece.

The method may further comprise rotating the battery and moving the battery connector. The battery may be rotated relative to the handpiece about the axis from the secured radial position to the initial radial position. The battery connector may be moved out of axial engagement with the handpiece connector at the initial radial position to remove the battery from the handpiece.

The method may further comprise providing a battery housing that includes an asymmetrical surface.

The method may yet further comprise providing a release mechanism in the battery housing with a button of the release mechanism being disposed on the asymmetrical surface.

A surgical system is shown at 30 in FIG. 1 for releasably securing a module 32 to a battery 34. As is described in greater detail below, the surgical system 30 is configured to facilitate both physical and electrical connections between the battery 34 and different types of modules 32 employed for use in surgical or medical procedures in a "twist-lock" manner.

Figure 2:
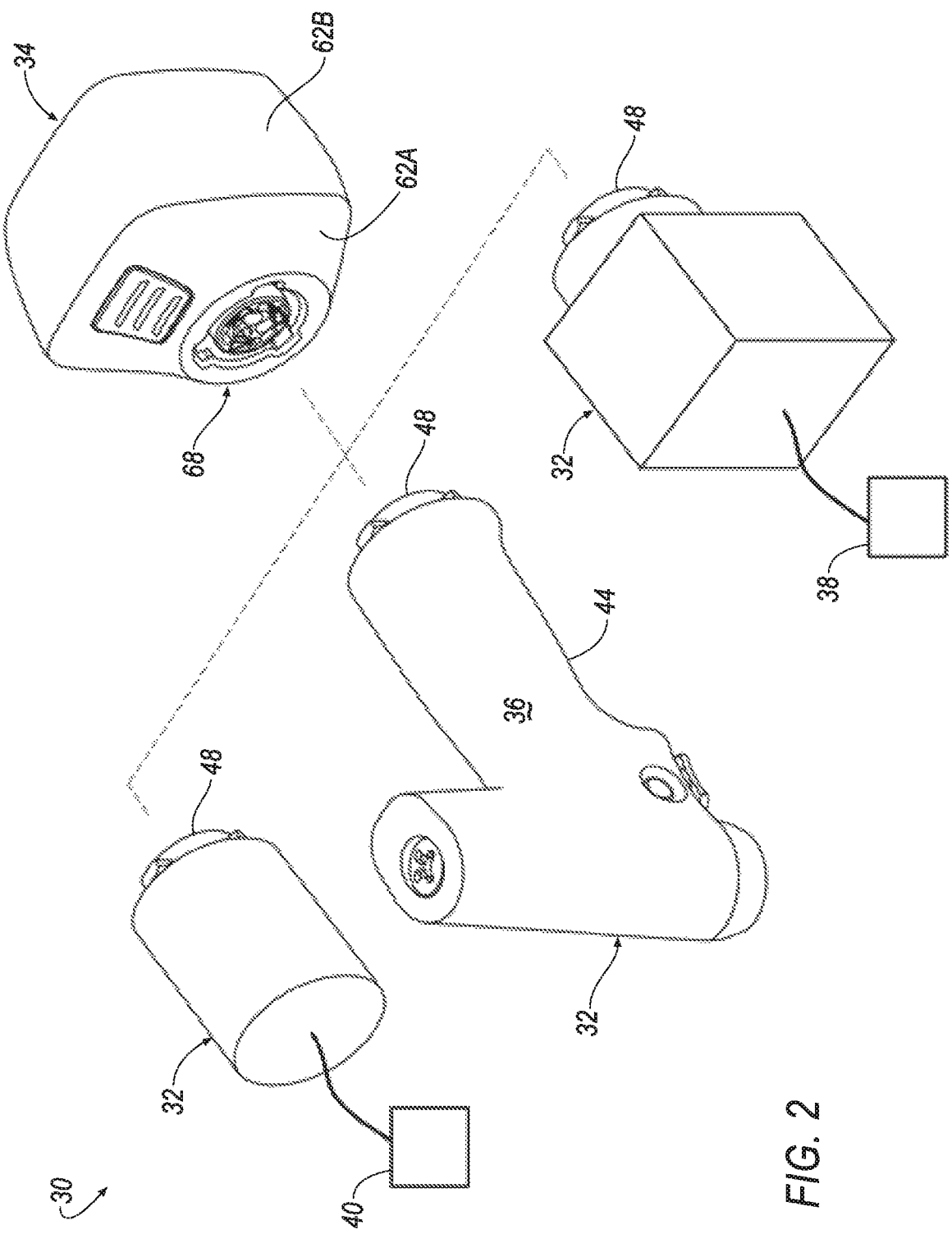
FIG. 2 is a perspective view of the system of FIG. 1, shown with the battery spaced from the handpiece and positioned adjacent to schematically illustrated additional modules adapted to connect to the battery.
Figure 3:
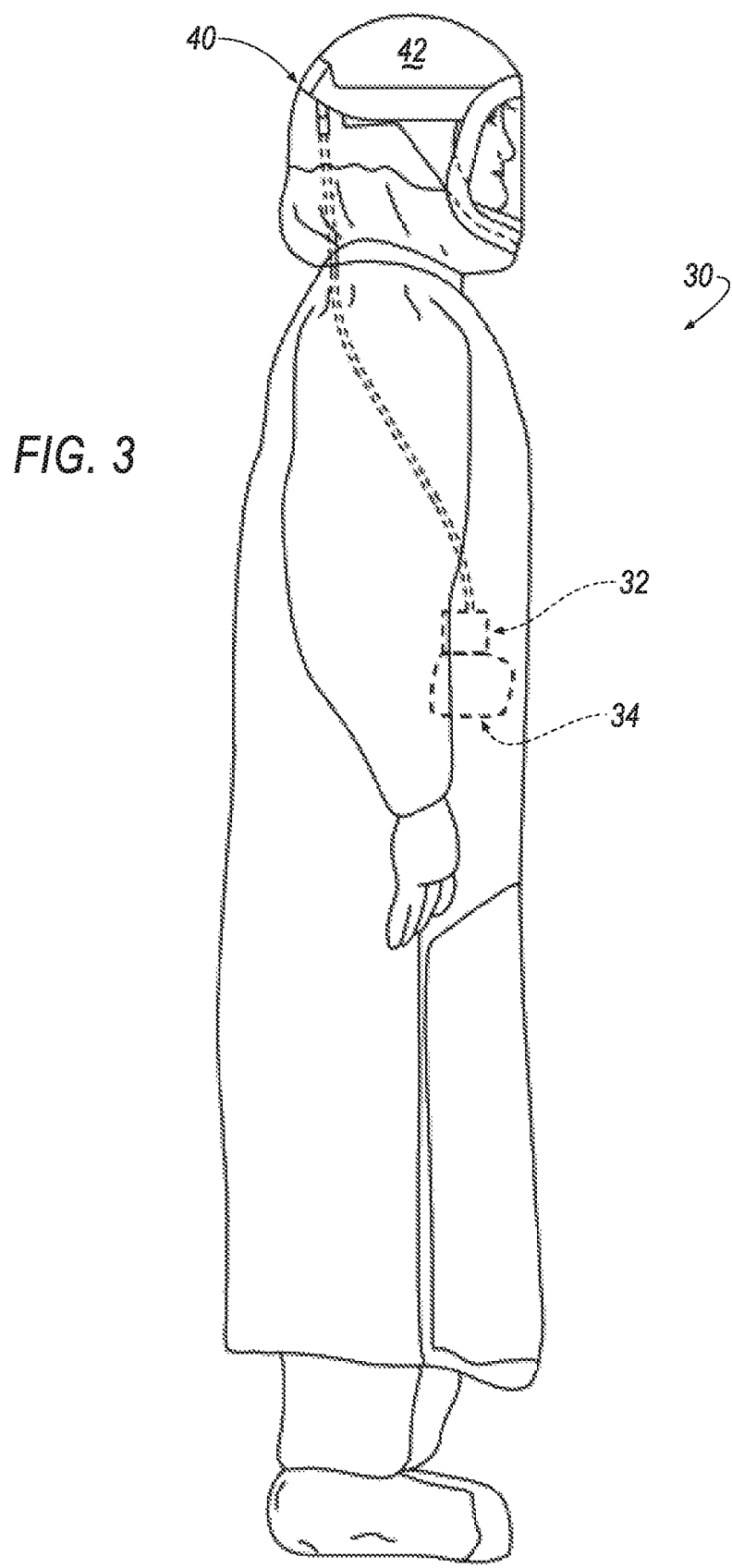
FIG. 3 is a right-side view of a user wearing a headpiece powered by the battery and employing one of the modules of FIG. 2.

As shown in FIG. 2, the module 32 may comprise a handpiece 36 for performing a surgical procedure, a charger 38, illustrated in part schematically, for storing an electric charge in the battery 34, or an instrument 40, illustrated in part schematically, powered by the battery 34 and otherwise adapted for use by medical professionals. In one representative example illustrated in FIG. 3, the instrument 40 is a tethered surgical headpiece which employs an air circulation system 42 that is powered by the battery 34. However, as will be appreciated from the further description of the surgical system 30 below, other types of instruments 40 which may be powered via the battery 34 are contemplated. By way of non-limiting example, instruments 40 may comprise lights, cameras, speakers, microphones, sensors, and the like. For the purposes of clarity and consistency, subsequent description of the module 32 will generally be made with reference to the handpiece 36, which is depicted throughout the drawings and which is described in greater detail below. Thus, unless otherwise indicated, the description of the various components and features of the handpiece 36 described herein also apply to other types of modules 32.

In the examples illustrated herein, one or more, or even all, of the various components of the surgical system 30 are "sterilizable," "autoclavable," or are otherwise capable of withstanding repeated steam sterilization in an autoclave, subjected to such as a temperature of 134 degrees Celsius for 3 minutes. Other sterilization or autoclave cycle parameters are contemplated.

The components of the surgical system 30 may also be configured to withstand chemical detergents used in cleaning medical/surgical equipment. In other examples, the battery 34 and the handpiece 36 may be configured to withstand all known sterilization and decontamination methods for medical equipment, or only specific sterilization methods and/or specific decontamination methods. In one example, "withstand" means experiencing decontamination conditions without melting, deformation, or decomposition. Certain methods for decontamination may include manual wash, automatic wash (such as with thermal disinfectant), steam sterilization, low-temperature sterilization (such as Sterrad®), chemical disinfection (for example, point-of-contact), chemical and mechanical cleaning (such as with detergents and microfiber materials), and the like.

The battery 34 is configured to be sterilized via steam sterilization, hydrogen peroxide sterilization, or other suitable sterilization technique. By "sterile," it is meant that, once the process is complete, the battery 34 has a sterilization assurance level (SAL) of at least $10^{-6}$. This means that there is equal to or less than one chance in a million that a single viable microorganism is present on the sterilized item. This definition of sterile is the definition set forth in the ANSIAAMI ST35-1966. Safe handling and biological decontamination of medical devices in health care facilities and nonclinical settings. For alternative applications, the "sterilization" process is sufficient if, once the process is complete, the battery 34 has a SAL of at least $10^{-4}$. It will be appreciated that other standards may be used to define the term "sterile" in some examples.

Referring now to FIGS. 1-10, as noted above, the handpiece 36 is employed in performing surgical procedures and is powered via the battery 34. It will be appreciated that the handpiece 36 can be of any suitable type or configuration suitable for use in connection with surgical procedures. By way of non-limiting example, the handpiece 36 could be realized as a drill, a sagittal saw, a stapler, and the like. The handpiece 36 generally comprises a body 44, a handpiece controller 46 (see FIG. 10), and a handpiece connector 48. Each of these components will be described in greater detail below.

The body 44 of the handpiece 36 has a generally pistol-shaped profile with a hand grip 50 and a chassis 52. The handpiece connector 48 is operatively coupled to the hand grip 50, such as with one or more fasteners 54, shown in FIG. 8, and is configured to releasably attach to the battery 34 as described in greater detail below. The chassis 52 of the body 44 supports an interface 56 that is configured to releasably secure a tool accessory such as a cutting implement, a drill bit, a burr, a saw, a blade, a staple cartridge, and the like. Because the handpiece 36 is illustrated generically throughout the drawings, those having ordinary skill in the art will appreciate that, depending on the specific configuration of the handpiece 36, the interface 56 may comprise a chuck, a reciprocating head, a staple driver, and the like.

Figure 10:
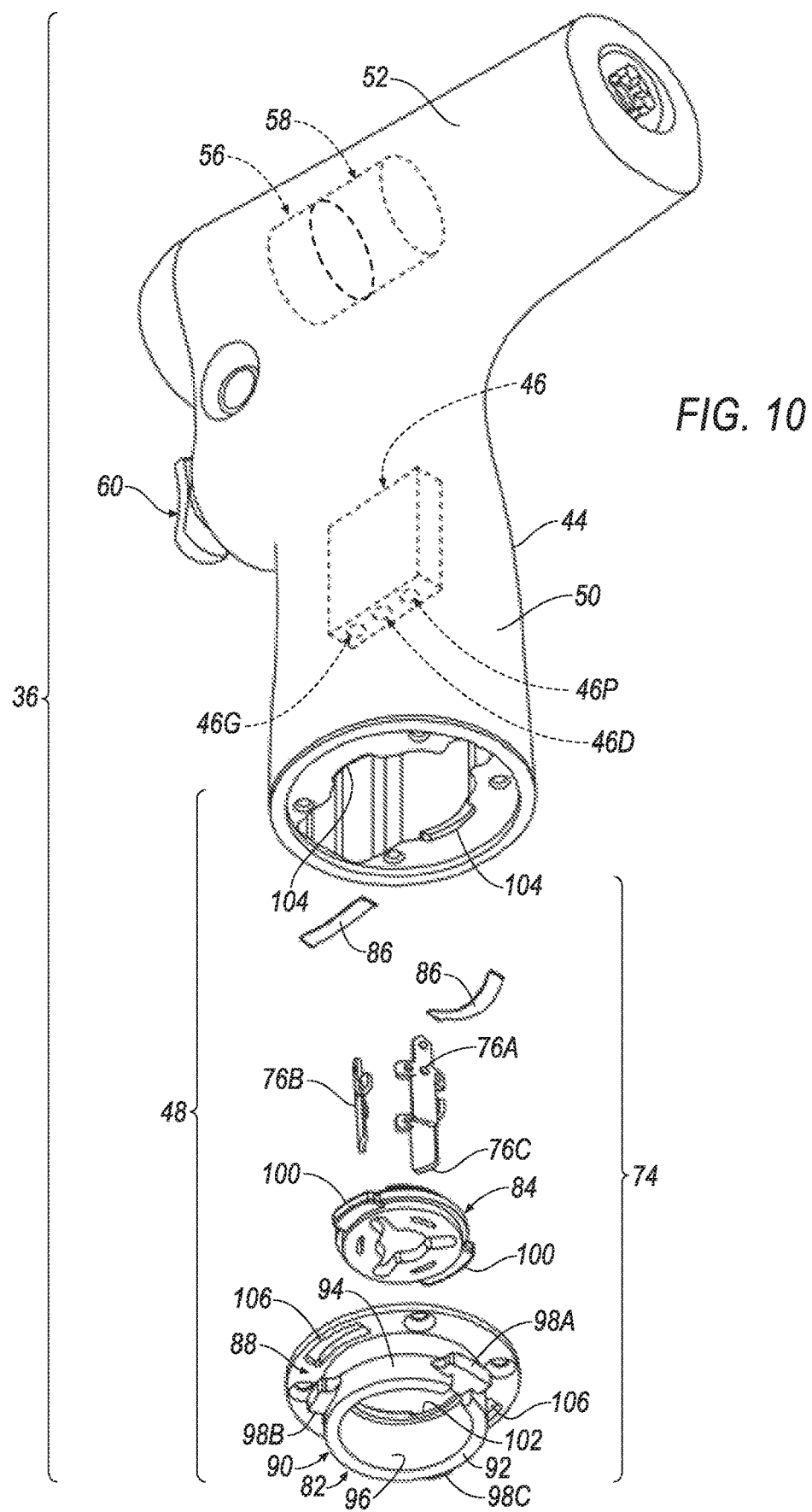
FIG. 10 is a partially-exploded perspective view of the handpiece of FIGS. 8-9, showing the handpiece connector, a pair of biasing elements, and a handpiece controller.

As shown in FIG. 10, the handpiece 36 also generally comprises a motor 58 and an input control 60, each of which are disposed in electrical communication with the handpiece controller 46 which, in turn, is supported within the body 44. The input control 60 has a trigger-style configuration, is responsive to actuation by the surgeon, and communicates with the handpiece controller 46. The motor 58 is coupled to the interface 56 and is configured to selectively generate rotational torque in response to commands, signals, and the like received from the handpiece controller 46. Thus, when the surgeon actuates the input control 60 to operate the handpiece 36, the handpiece controller 46 directs power from the battery 34 to the motor 58 which, in turn, drives the interface 56. Those having ordinary skill in the art will appreciate that the body 44, the handpiece controller 46, the interface 56, the motor 58, and the input control 60 could each be configured in a number of different ways sufficient to facilitate operation of the handpiece 36 via power from the battery 34.

Figure 6:
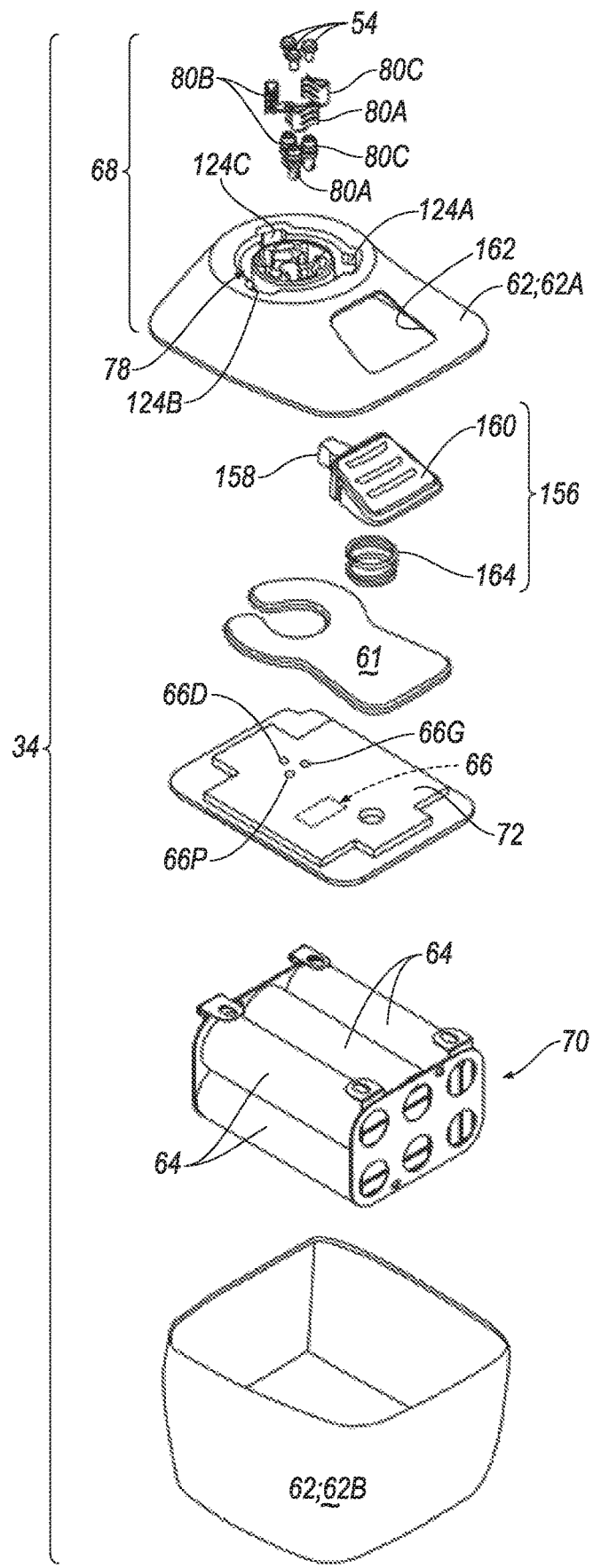
FIG. 6 is a partially-exploded perspective view of the battery of FIGS. 1-5, showing the battery connector, a release mechanism, a seal, a battery controller, a cell, and a pair of housing components.
Figure 7:
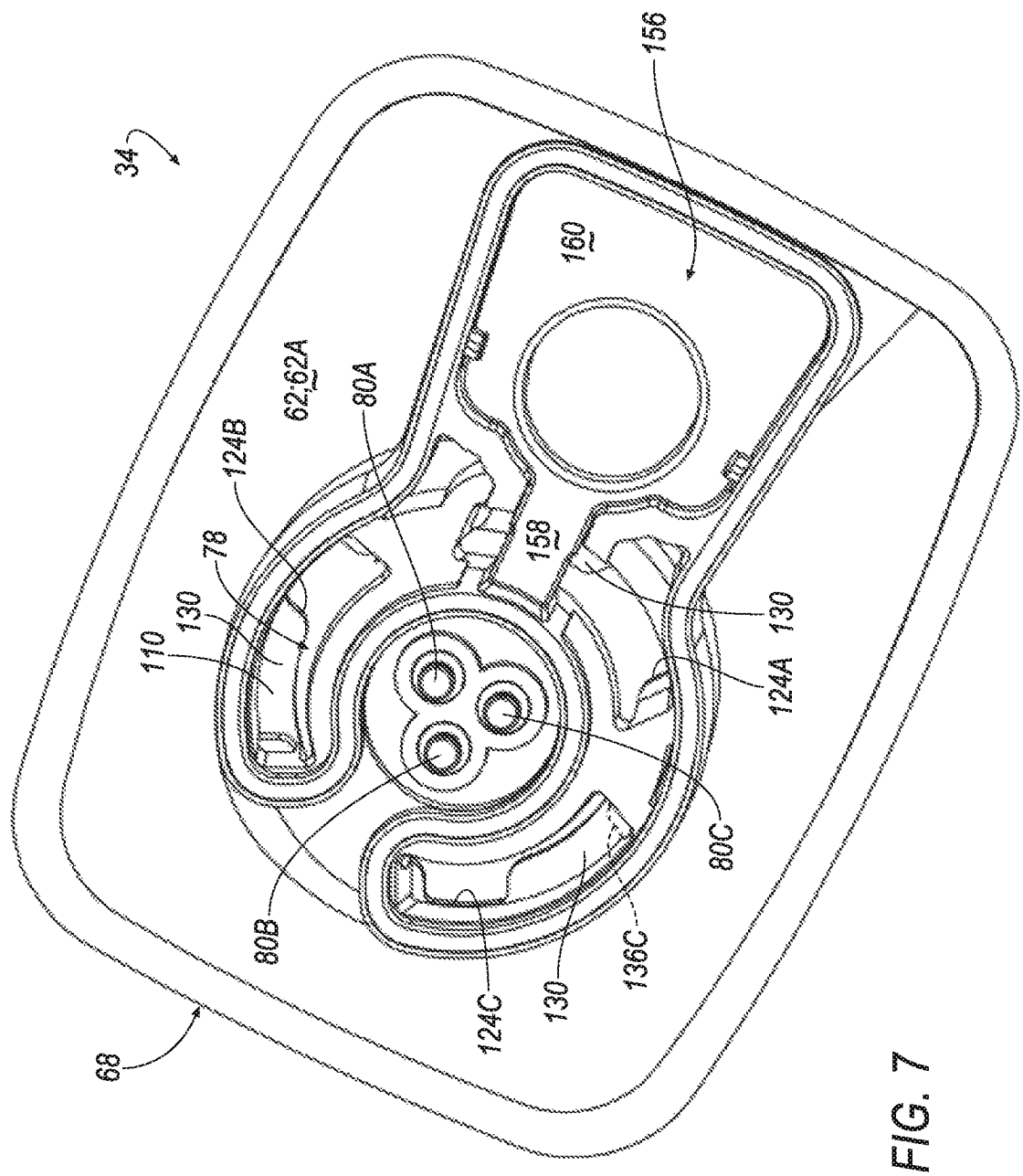
FIG. 7 is a bottom perspective view showing portions of the battery connector, the release mechanism, and one of the housing components of FIG. 6.

As noted above, the battery 34 provides a source of electrical power to the handpiece 36. To this end, and as is best shown in FIG. 6, the battery 34 generally comprises a housing 62, a rechargeable cell 64 for storing an electric charge, a battery controller 66, and a battery connector 68 operatively coupled to the housing 62 and configured to releasably attach to the handpiece connector 48. Each of these components will be described in greater detail below. In one of the representative examples illustrated herein, the housing 62 of the battery 34 comprises first and second housing components 62A, 62B which cooperate to support the various components of the battery 34. The first housing component 62A also defines certain parts of the battery connector 68 in the illustrated example. However, those having ordinary skill in the art will appreciate from the subsequent description below that the battery connector 68 could be formed separately from and operatively coupled to the housing 62.

It will be appreciated that the first and second housing components 62A, 62B can be attached to each other in a number of different ways sufficient to form a seamless bond capable of withstanding repeated sterilization, such as with the use of interlocking structural features, fasteners, adhesive, welding, and the like. Moreover, one or more gaskets, seals, O-rings, and the like which are formed of a sterilizable (e.g., autoclavable, aseptically sterilizable) and/or compressible material (for example, EDPM rubber or silicone rubber) may be disposed between the first and second housing components 62A, 62B to form a hermetic barrier therebetween. It will be appreciated that the housing 62 of the battery 34 may comprise a material suitable for autoclave cycles, including, but not limited to polyether ether ketone, polyetherimide, polyphenylsulfone, and the like. One type of seal 61 is depicted in FIG. 6. Other types and arrangements of seals are contemplated.

While many versions of the battery 34 include a housing 62 that is sterilizable, sealed, and supports the cells 64, the battery controller 66, and other components of the battery 34 therein, it will be appreciated that the battery 34 could be designed differently in certain examples. For example, the battery 34 could be realized as an "aseptic battery," which employs a non-sterilizable cell cluster with a circuit board that supports electrical components such as cell regulators, FETS, resistors, capacitors, and processors, and the like. Here, the cell cluster can be removably fitted into a housing that is sterilizable. Once the cell cluster is fitted in the housing, the housing is sealed to encapsulate the cell cluster in a sterilized enclosure. A further understanding of the structure of an aseptic battery assembly can be obtained from U.S. Pat. No. 7,705,559/PCT Pub. No. WO 2007/090025 A1, the contents of which are incorporated herein by reference. See also SYSTEM AND METHOD FOR RECHARGING A BATTERY EXPOSED TO A HARSH ENVIRONMENT, filed Oct. 21, 2005, the contents of which are published in U.S. Pat. Pub. No US 2007/0090788 incorporated herein by reference.

In the illustrated example, the battery 34 comprises a plurality of cells 64 which cooperate to define a pack 70. It will be appreciated that the cells 64 can be arranged in different ways to achieve specific power output requirements of the pack 70, such as by wiring each cell 64 in series to increase the potential difference across the pack 70 above the potential difference across a single cell 64. However, those having ordinary skill in the art will appreciate that the battery 34 could employ any suitable number of discrete cells 64 and/or packs 70 of cells 64, arranged or disposed in any suitable way sufficient to provide a source of electrical power to the handpiece 36, including cells 64 connected together in parallel. Furthermore, it will be appreciated that the cells 64 could be of any type or configuration sufficient to store electrical charge. The cells 64 may be realized as "high-temperature" cells 64 configured to sustain functionality without damage during sterilization cycles. For example, the cells 64 may be any suitable nickel or lithium chemistry cell, including but not limited to lithium ion ceramic cells, lithium iron phosphorous oxynitride cells, lithium tin phosphorous sulfide cells, and the like. The cells 64 may include thermal insulation to minimize damage incurred during sterilization cycles. The thermal insulation may comprise an aerogel, such as polyimide, silica, or carbon aerogel.

The pack 70 of cells 64 is disposed in electrical communication with the battery controller 66 which, in turn, is disposed in electrical communication with the battery connector 68. Here, it will be appreciated that electrical communication can be achieved in a number of different ways, such as by soldering, wiring, physical contact between conductive materials, and the like. In the example illustrated in FIG. 6, the battery controller 66 is arranged on a printed circuit board 72 which is configured to be electrically connected to the battery cell pack 70 via battery straps (e.g., thin pieces of electrically conductive material, not shown). The straps may be fixedly electrically connected (e.g., soldered, welded) to the pack 70. The straps may engage electrical contact pads (not shown) on the printed circuit board 72 for electrical connection between the pack 70 and the printed circuit board 72. The contact pads may be wired to the battery connector 68 (wires not shown). Other arrangements are contemplated. For example, the battery controller 66 could be spaced from the printed circuit board 72. Similarly, while the printed circuit board 72 is coupled to the pack 70 in the illustrated example, the printed circuit board 72 could be spaced from the pack 70 and mounted separately to the housing 62.

The handpiece controller 46 (see FIG. 10) and the battery controller 66 (see FIG. 6) cooperate to effect operation of the handpiece 36 in use. In some examples, the handpiece controller 46 is configured to facilitate operation of the handpiece 36 based on different operating conditions, parameters, and the like of the battery 34 and/or the handpiece 36. By way of non-limiting example, the handpiece controller 46 may be configured to limit, restrict, or otherwise adjust operation of the handpiece 36 based on status conditions of the battery 34 such as voltage, current draw, internal resistance, number of charge cycles, amount of time since the previous charge, and the like, as well as characteristics which identify the battery 34 or distinguish it from other batteries 34 such as manufacture or service date, serial or product number, firmware version, charge capacity, and the like. To these ends, the handpiece controller 46 has a handpiece power connection 46P, a handpiece ground connection 46G, and a handpiece data connection 46D; and the battery controller 66 has a corresponding battery power connection 66P, a battery ground connection 66G, and a battery data connection 66D. The handpiece connections 46P, 46G, 46D are configured to be disposed in respective electrical communication with the battery connections 66P, 66G, 66D when the handpiece 36 is properly secured to the battery 34 via the engagement between the handpiece connector 48 and the battery connector 68, as described in greater detail below.

Some batteries 34 are also provided with supplemental components, such as internal sensors, data collection circuits, memories, control processors, and the like. These components may monitor the environment to which the battery 34 is exposed, store data regarding the use of the battery 34, or store data regarding the handpiece 36 to which the battery 34 is attached. When a battery 34 is provided with one of these supplemental components, signals may be received from and/or transmitted to the supplemental components across the battery data connection 66D. The Applicant has disclosed batteries that include these types of supplemental components in U.S. Pat. No. 6,018,227, BATTERY CHARGER ESPECIALLY USEFUL WITH STERILIZABLE RECHARGEABLE BATTERY PACKS, issued on Jan. 25, 2000, and U.S. Pat. No. 9,419,462 B2/PCT Pub. No. WO 2007/050439 A2, SYSTEM AND METHOD FOR RECHARGING A BATTERY EXPOSED TO A HARSH ENVIRONMENT, published on Apr. 26, 2007, the contents of both which are incorporated herein by reference.

While the example illustrated herein is directed toward facilitating electrical communication between the handpiece 36 and the battery 34 via physical contact across the handpiece connector 48 and the battery connector 68, it will be appreciated that electrical communication can be effected in a number of different ways. By way of non-limiting example, electrical communication between the handpiece data connection 46D and the battery data connection 66D could be effected using transmitters and receivers configured to exchange data and/or information wirelessly. To this end, one or more of Near Field Communication (NFC), Radio Frequency Identification (RFID), Wi-Fi®, Bluetooth®, and the like could be used to facilitate wireless communication between the handpiece data connection 46D of the handpiece 36 and the battery data connection 66D of the battery 34.

As described in greater detail below, physical contact between the handpiece connector 48 and the battery connector 68 is employed to facilitate transferring electrical power from the battery 34 to the secured handpiece 36 via the handpiece and battery power connections 46P, 66P and the handpiece and battery ground connections 46G, 66G. This physical contact can also be used to charge the battery 34 where the module 32 is a charger 38 that connects to the battery connector 68 in the same way as the handpiece connector 48 (see FIG. 2). However, those having ordinary skill in the art will appreciate that the battery 34 can be charged in different ways, such as without the use of a physical electrical connection with the charger 38 in contact with the battery connector 68. By way of non-limiting example, the battery 34 could employ a charging coil (not shown) configured to facilitate wireless, inductive charging. Other configurations are contemplated.

As noted above, the surgical system 30 is configured to facilitate both physical and electrical connections between the battery 34 and the handpiece 36 via the battery connector 68 and the handpiece connector 48 in a "twist-lock" manner.

Figure 4:
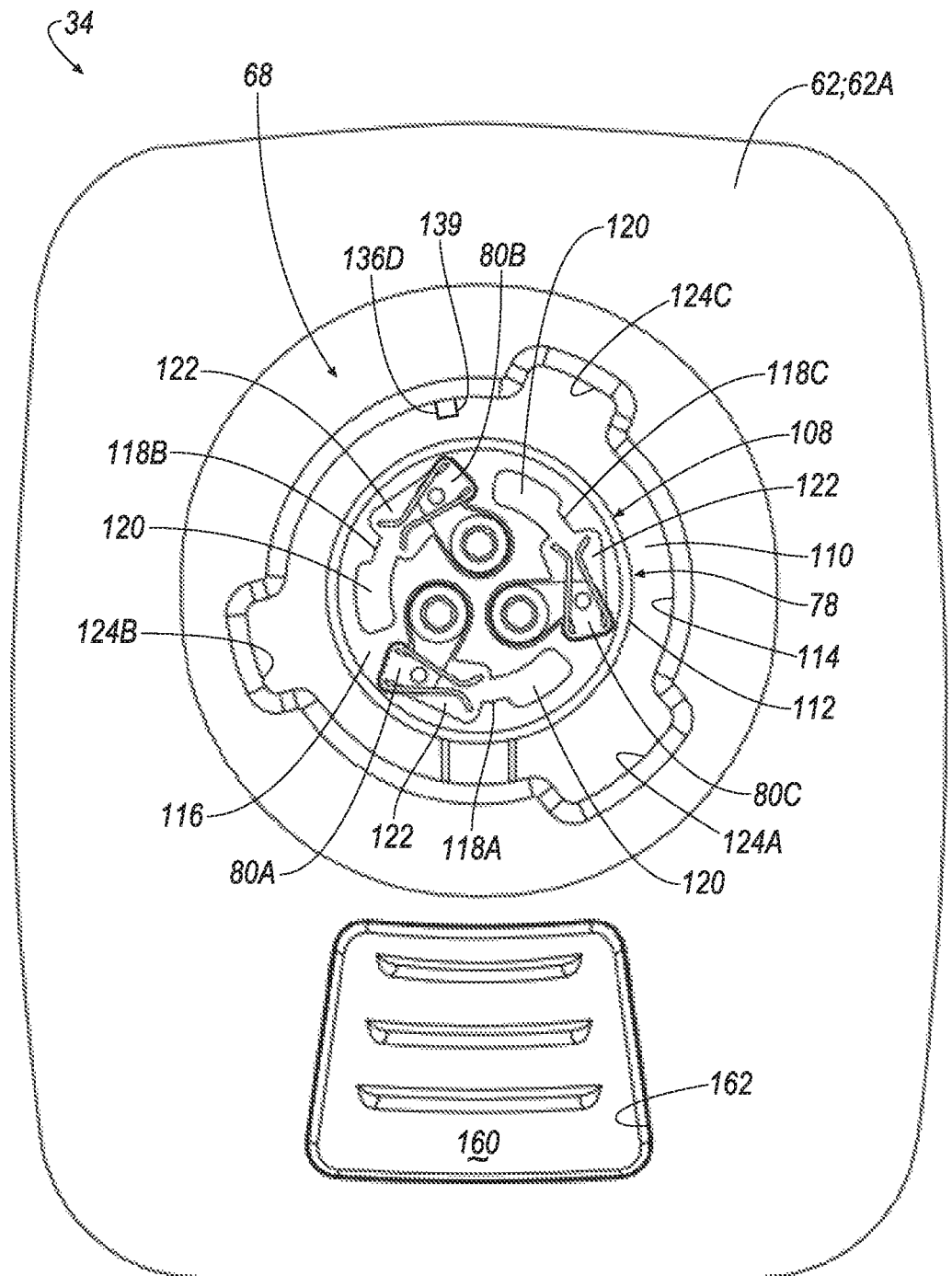
FIG. 4 is a top-side view of the battery of FIGS. 1-3, shown having a battery connector according to one example.
Figure 5:
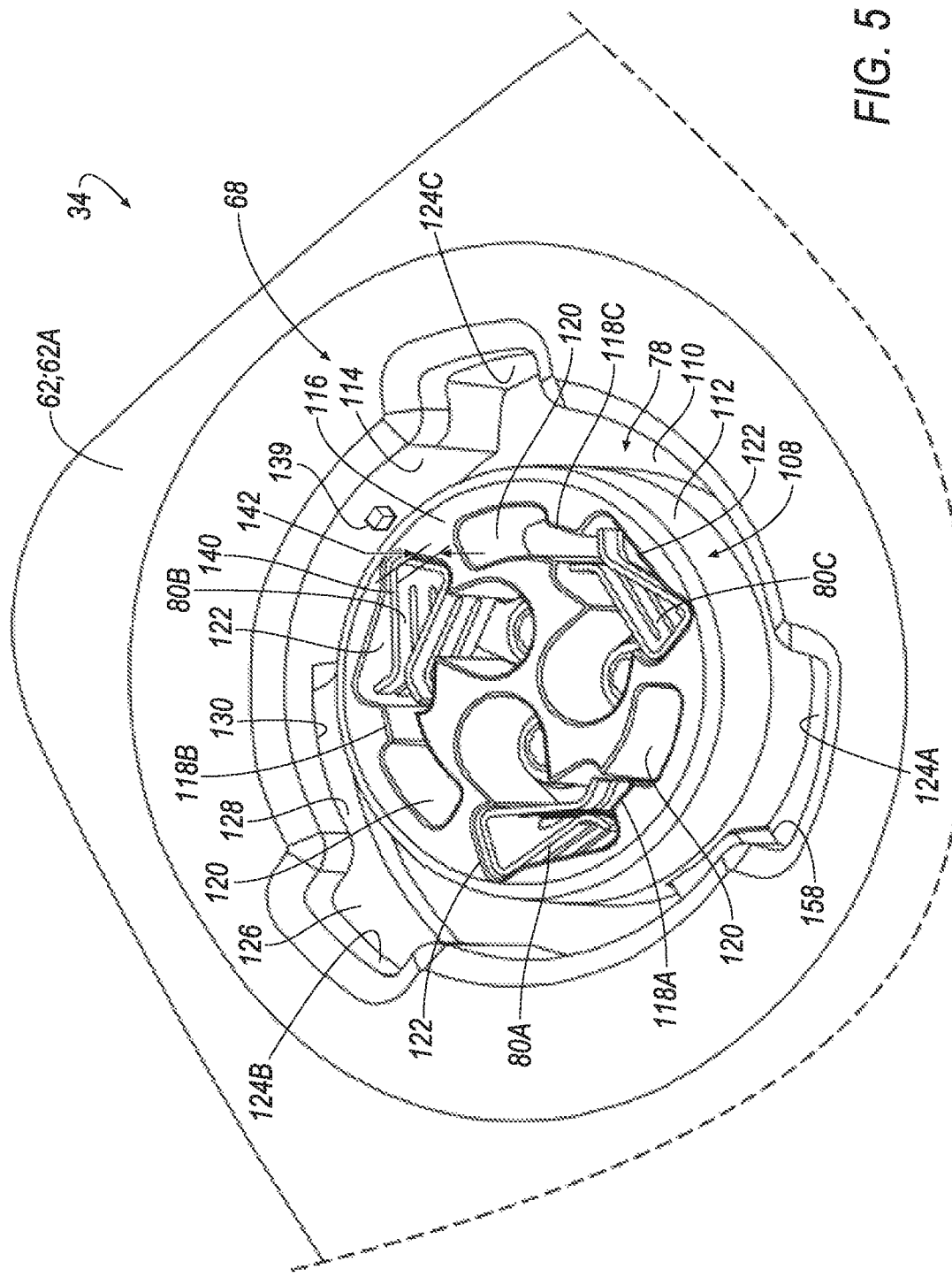
FIG. 5 is a partial perspective view showing additional detail of the battery connector of FIG. 4.
Figure 8:
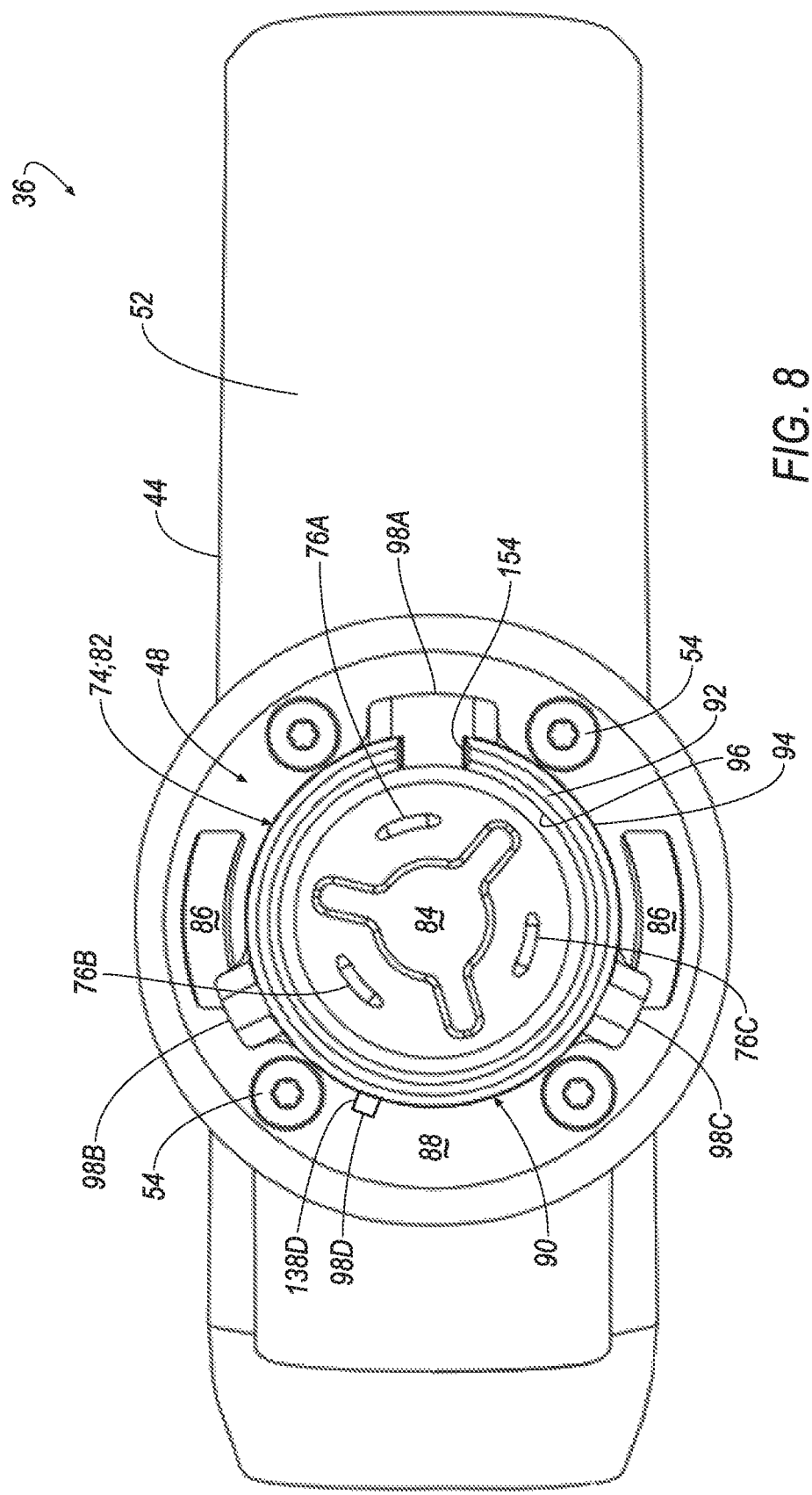
FIG. 8 is a bottom-side view of the handpiece of FIGS. 1-2, shown having a handpiece connector according to one example.
Figure 9:
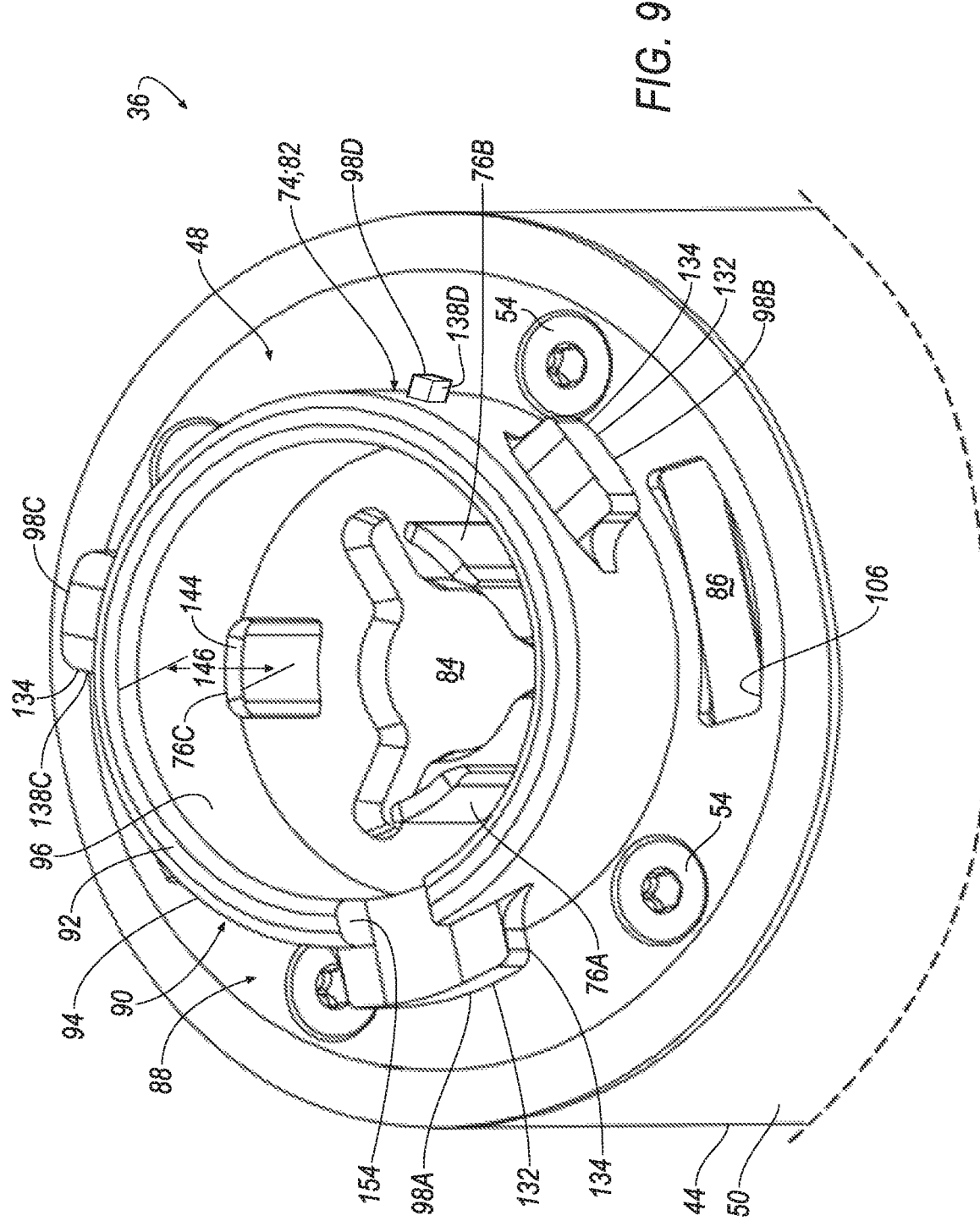
FIG. 9 is a partial perspective view showing additional detail of the handpiece connector of FIG. 8.

To this end, and as is best depicted in FIGS. 8-10, the handpiece connector 48 comprises a first coupler 74, a first handpiece terminal 76A, a second handpiece terminal 76B, and a third handpiece terminal 76C. The first handpiece terminal 76A and the third handpiece terminal 76C may alternatively be respectively characterized as the handpiece power terminal 76A and the handpiece ground terminal 76C. Yet alternatively, terminals 76A and 76C may be generically identified as handpiece voltage terminals 76A and 76C. The second handpiece terminal 76B may be alternatively identified as the handpiece data terminal 76B. Similarly, as best depicted in FIGS. 4-6, the battery connector 68 comprises a second coupler 78 configured to rotatably engage the first coupler 74, a first battery terminal 80A, a second battery terminal 80B, and a third battery terminal 80C. The first battery terminal 80A and the third battery terminal 80C may alternatively be respectively characterized as the battery power terminal 80A and the battery ground terminal 80C. Yet alternatively, terminals 80A and 80C may be generically identified as battery voltage terminals 80A and 80C. The second battery terminal 80B may be alternatively identified as the battery data terminal 80B. Each of these components will be described in greater detail below.

Figure 11A:
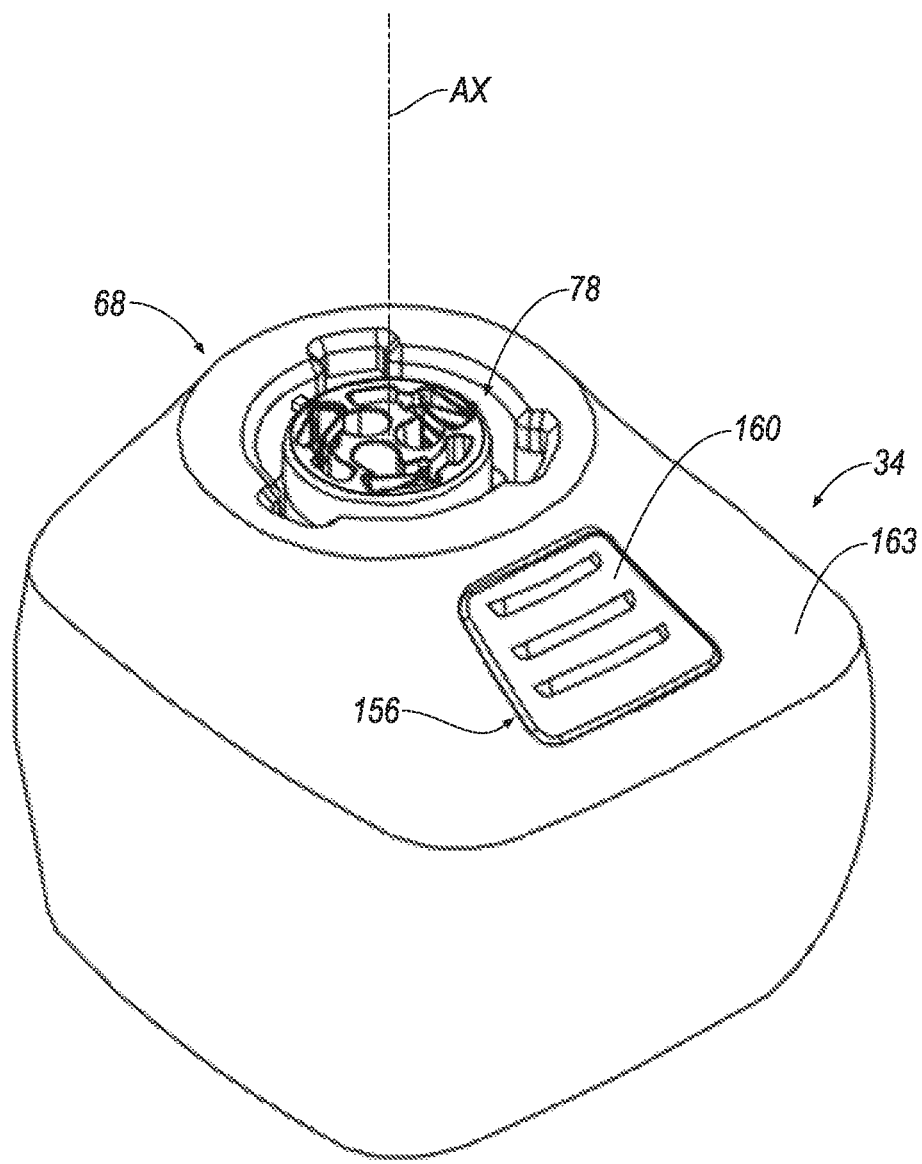
FIG. 11A is a perspective view of the battery of FIGS. 1-7.
Figure 11B:
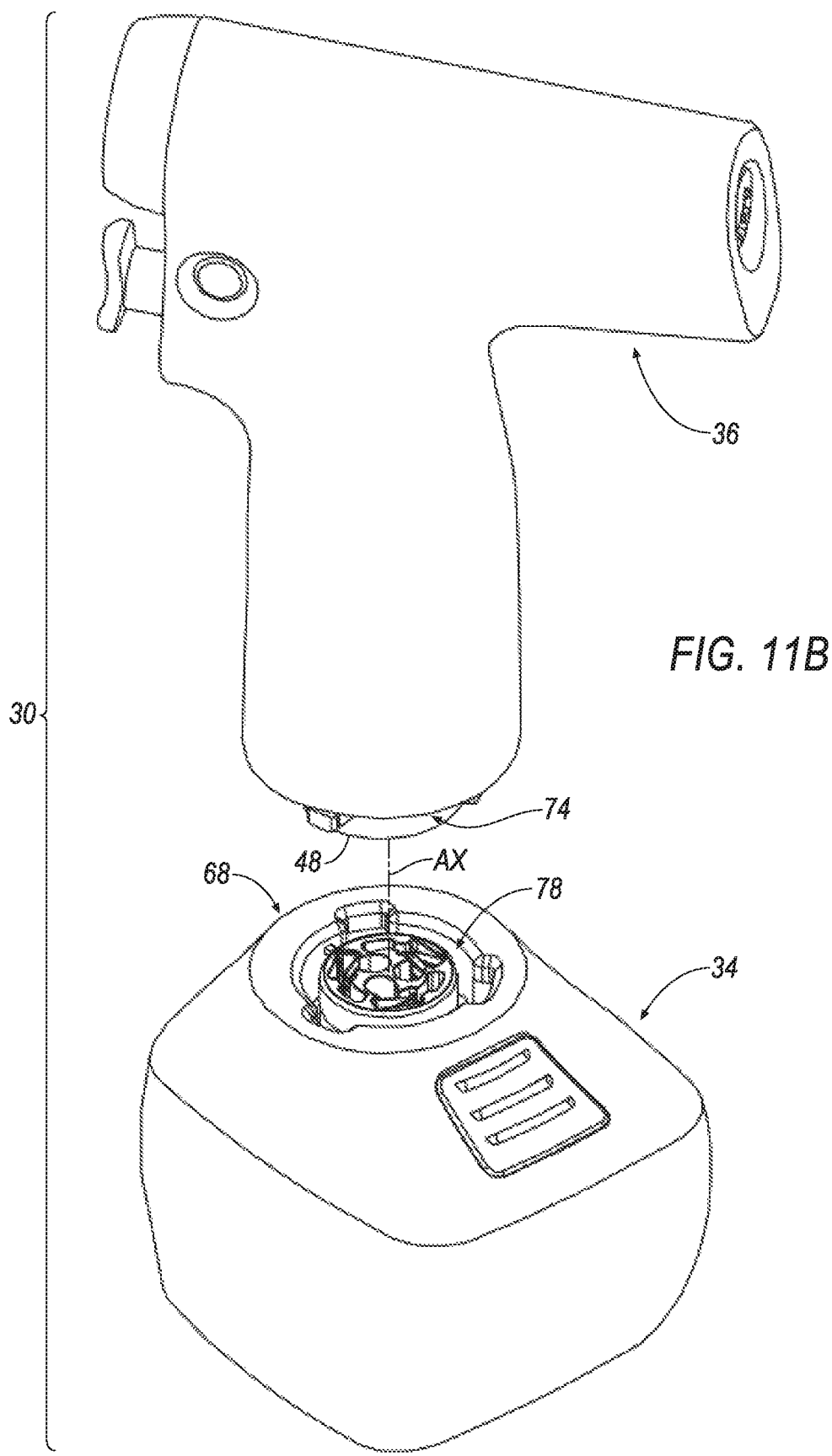
FIG. 11B is another perspective view of the battery of FIG. 11A, showing the handpiece of FIGS. 1-2 and 8-10 positioned above the battery with the handpiece connector facing and aligned with the battery connector at an initial radial position.
Figure 11C:
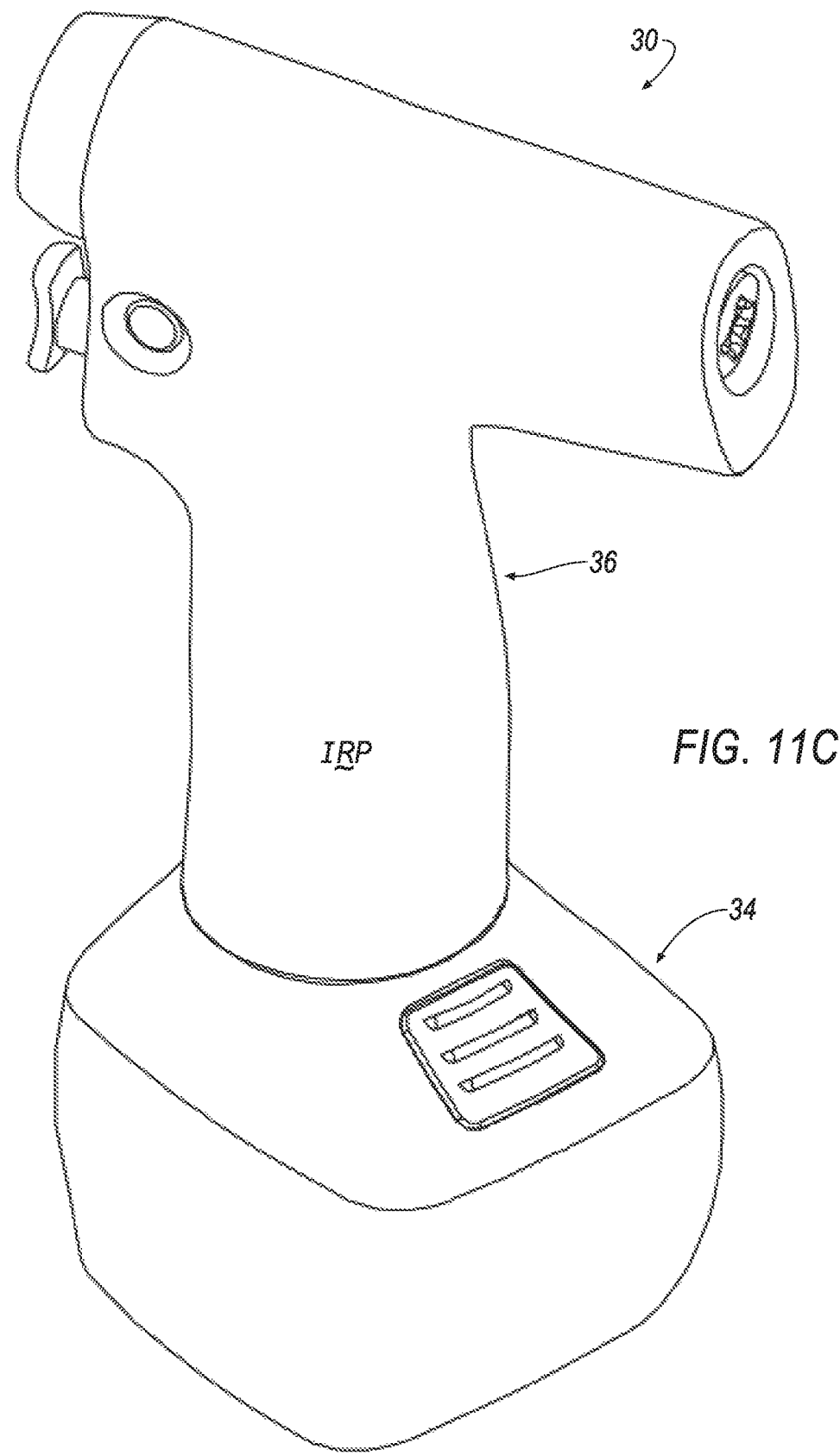
FIG. 11C is another perspective view of the battery and the handpiece of FIG. 11B, shown with the handpiece connector engaging the battery connector at the initial radial position.

Referring now to FIGS. 11A-11E, certain steps are depicted sequentially for effecting the "twist-lock" connection between the battery 34 and the handpiece 36. FIG. 11A shows a perspective view of the battery 34, with the second coupler 78 of the battery connector 68 defining an axis AX about which the battery terminals 80A, 80B, 80C are arranged. FIG. 11B shows the handpiece 36 positioned above the battery 34 with the first coupler 74 of the handpiece connector 48 aligned about the axis AX and arranged at an initial radial position IRP relative to the battery connector 68. FIG. 11C shows the handpiece 36 moved toward the battery 34 along the axis AX while still arranged in the initial radial position IRP (compare FIG. 11C to FIG. 11B). As is described in greater detail below, the second coupler 78 is configured to receive the first coupler 74 at the initial radial position IRP and to permit relative axial movement between the battery 34 and the handpiece 36 along the axis AX at the initial radial position IRP.

Figure 11D:
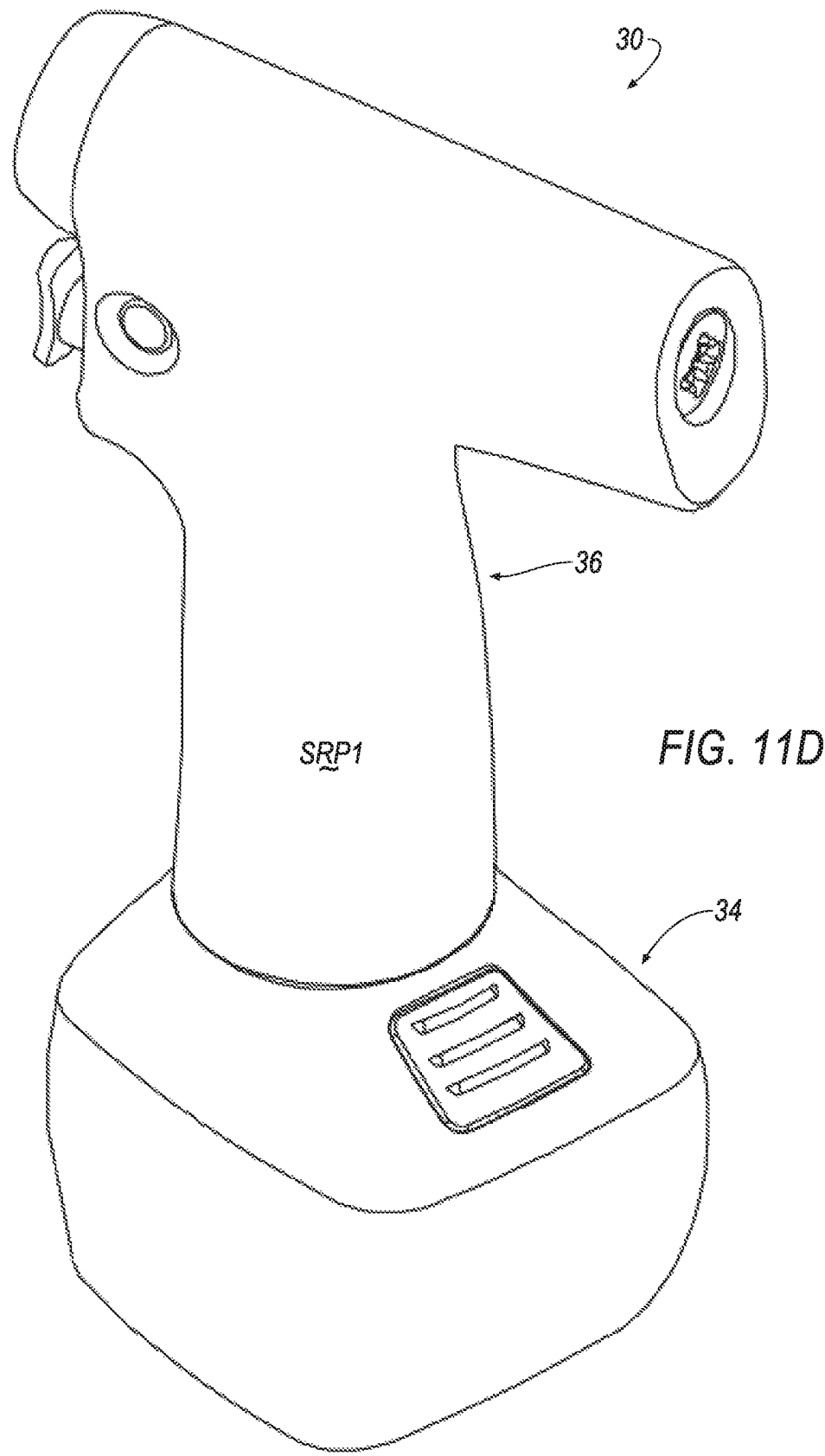
FIG. 11D is another perspective view of the battery and the handpiece of FIG. 11C, shown with the handpiece connector rotated from the initial radial position to one secured radial position relative to the battery connector.
Figure 11E:
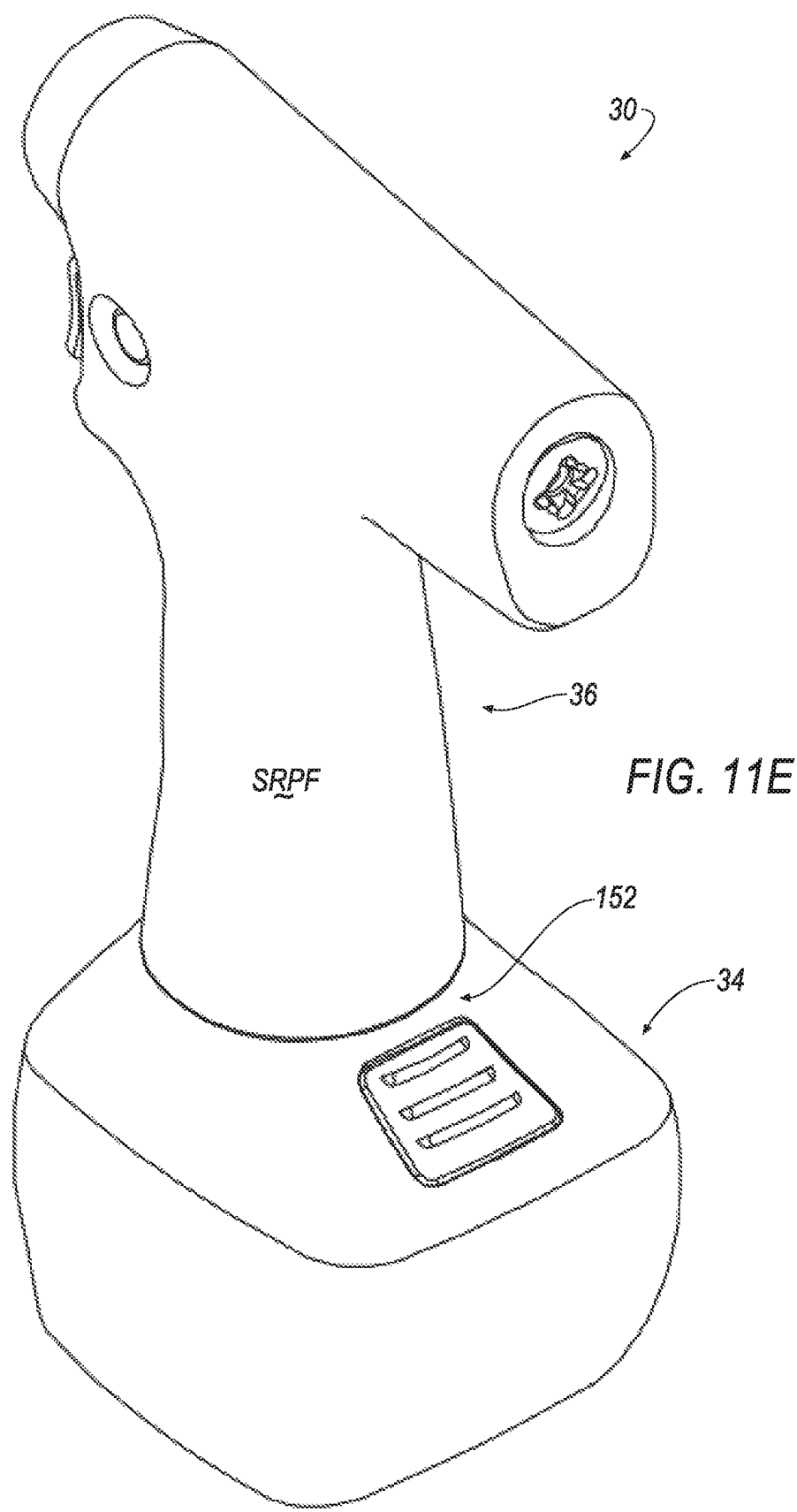
FIG. 11E is another perspective view of the battery and the handpiece of FIG. 11D, shown with the handpiece connector rotated further to another secured radial position relative to the battery connector.

Once the battery connector 68 receives the handpiece connector 48 at the initial radial position IRP as depicted in FIG. 11C, rotation of the battery 34 relative to the handpiece 36 is permitted from the initial radial position IRP to a plurality of different secured radial positions, depicted in FIGS. 11D-11E, where relative axial movement between the battery 34 and the handpiece 36 is constrained, including a first secured radial position SRP1 (see FIGS. 11D and 12C), a second secured radial position SRP2 (see FIG. 12D), and a final secured radial position SRPF (see FIGS. 11E and 12E), each of which will be described in greater detail below in connection with FIGS. 12A-12E. Additional secured positions are contemplated.

Figure 12A:
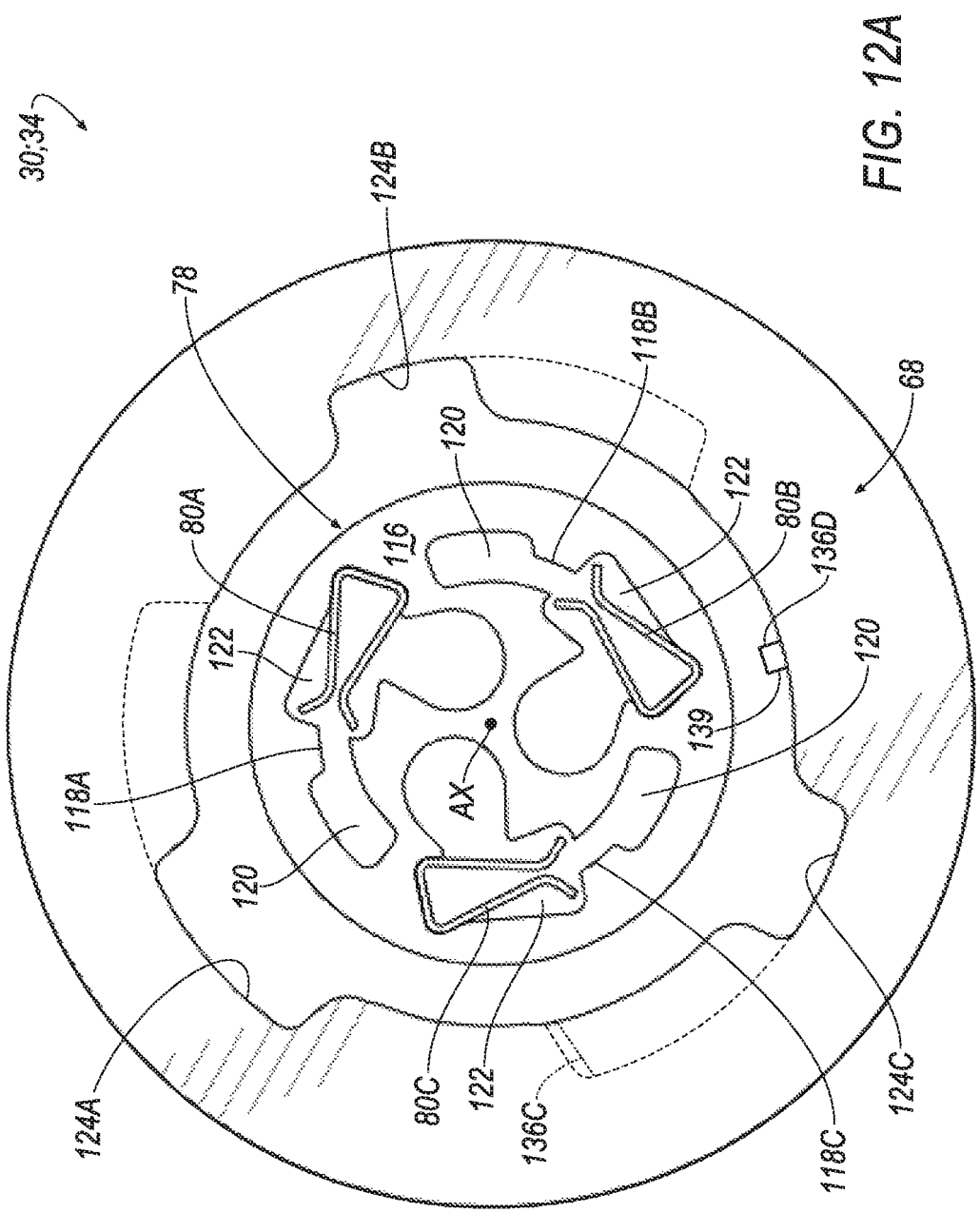
FIG. 12A is a schematic representation depicting the battery connector of FIG. 11A.
Figure 12D:
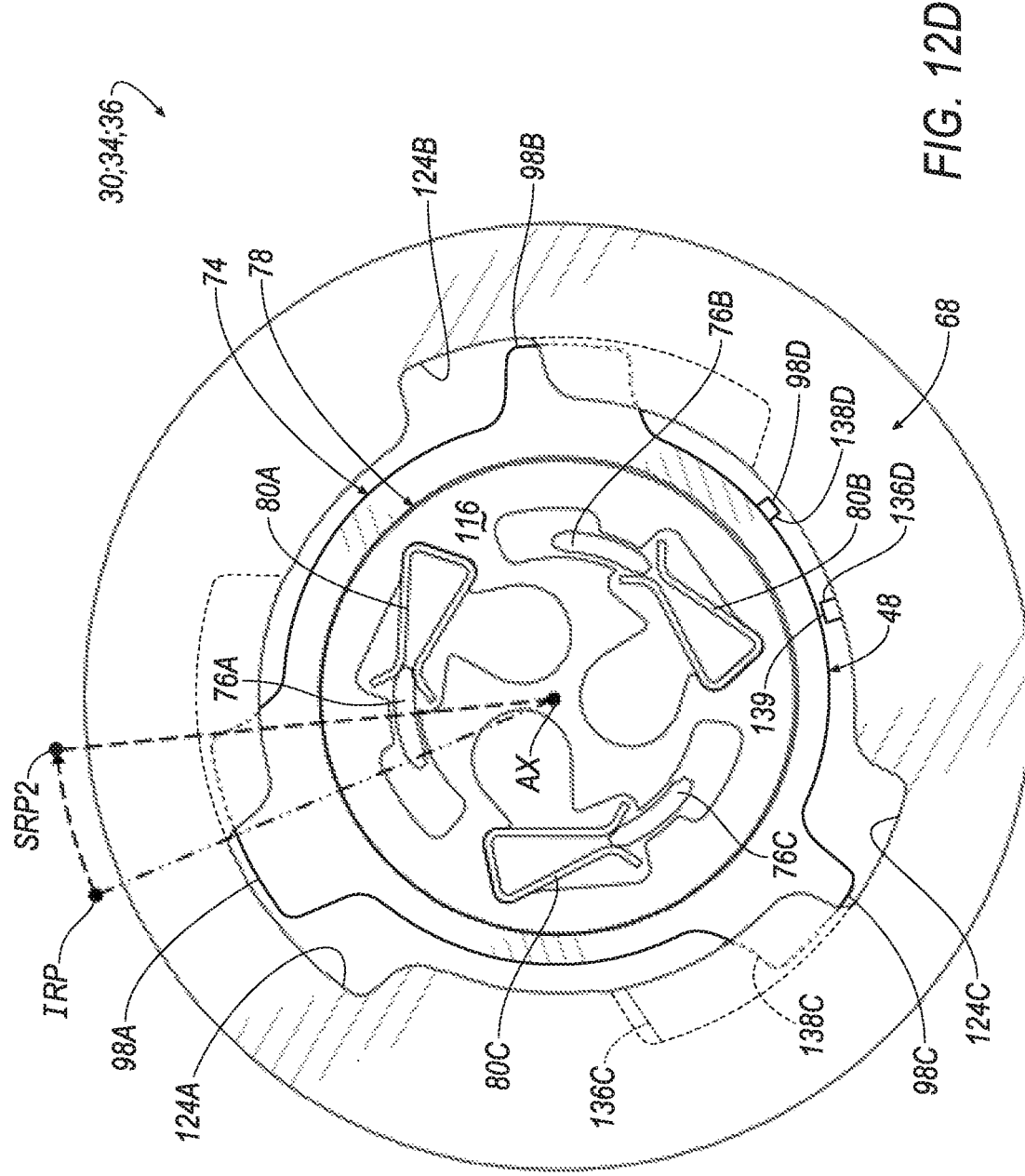
FIG. 12D is another schematic representation depicting engagement of the battery connector and the handpiece connector of FIG. 12C, shown with the handpiece connector rotated further to another secured radial position relative to the battery connector.

In the example illustrated throughout the drawings, the first secured radial position SRP1 is defined by initial engagement occurring between the first handpiece terminal 76A and the first battery terminal 80A (see FIG. 12C), and the second secured radial position SRP2 is defined by initial engagement occurring between the second handpiece terminal 76B and the second battery terminal 80B (see FIG. 12D). However, as will be appreciated from the subsequent description below, the first and second secured radial positions SRP1, SRP2 can be defined in a number of different ways, based on any suitable orientation between the handpiece connector 48 and the battery connector 68 where relative axial movement between the battery 34 and the handpiece 36 is constrained.

Referring now to FIGS. 4-12E, the handpiece terminals 76A, 76B, 76C of the handpiece connector 48, and the battery terminals 80A, 80B, 80C of the battery connector 68, are each arranged such that rotation from the initial radial position IRP, where the second coupler 78 receives the first coupler 74 (see FIG. 12B), to the first secured radial position SRP1 (see FIG. 12C) brings the first handpiece terminal 76A into engagement with the first battery terminal 80A, and rotation from the first secured radial position SRP1 (see FIG. 12C) to the second secured radial position SRP2 (see FIG. 12D) brings the second handpiece terminal 76B into engagement with the second battery terminal 80B while maintaining engagement between the first handpiece terminal 76A and the first battery terminal 80A. Thus, engagement of the first terminals 76A, 80A occurs before engagement of the second terminals 78B, 80B during rotation of the battery 34 relative to the handpiece 36. In the illustrated example, engagement of the third terminals 76C, 80C occurs concurrently with the first terminals 76A, 80A and, thus, likewise occurs before engagement of the second terminals 78B, 80B.

It will be appreciated that the arrangement of the terminals 76A, 76B, 76C, 80A, 80B, 80C described above ensures that electrical communication between the handpiece 36 and the battery 34 occurs in a specific sequence. By way of non-limiting example, in one example, the first handpiece terminal 76A, i.e., the handpiece power terminal, is electrically coupled to the handpiece power connection 46P, and the first battery terminal 80A, i.e., the battery power terminal, is electrically coupled to the battery power connection 66B; the second handpiece terminal 76B, i.e., the handpiece data terminal, is electrically coupled to the handpiece data connection 46D, and the second battery terminal 80B, i.e., the battery data terminal, is electrically coupled to the battery data connection 66D; and the third handpiece terminal 76C, i.e., the handpiece ground terminal, is electrically coupled to the handpiece ground connection 46G, and the third battery terminal 80C, i.e., the battery ground terminal, is electrically coupled to the battery ground connection 66G. Here, rotation from the initial radial position IRP (see FIG. 12B) to the first secured radial position SRP1 (see FIG. 12C) brings the first handpiece terminal 76A into engagement with the first battery terminal 80A to electrically couple the handpiece power connection 46P and the battery power connection 66P, and brings the third handpiece terminal 76C into engagement with the third battery terminal 80C to electrically couple the handpiece ground connection 46G and the battery ground connection 66G. However, in the initial radial position IRP, the second handpiece terminal 76B remains out of engagement with the second battery terminal 80B to prevent electrical communication from occurring between the handpiece data connection 46D and the battery data connection 66D at the first secured radial position SRP1. Put differently, power and ground connections are established between the battery 34 and the handpiece 36 to enable the transmission of power between the cell 64 and the handpiece controller 48 prior to data being communicated between the battery 34 and the handpiece 36, which occurs after subsequent rotation from the first secured radial position SRP1 (see FIG. 12C) to the second secured radial position SRP2 (see FIG. 12D).

Figure 13:
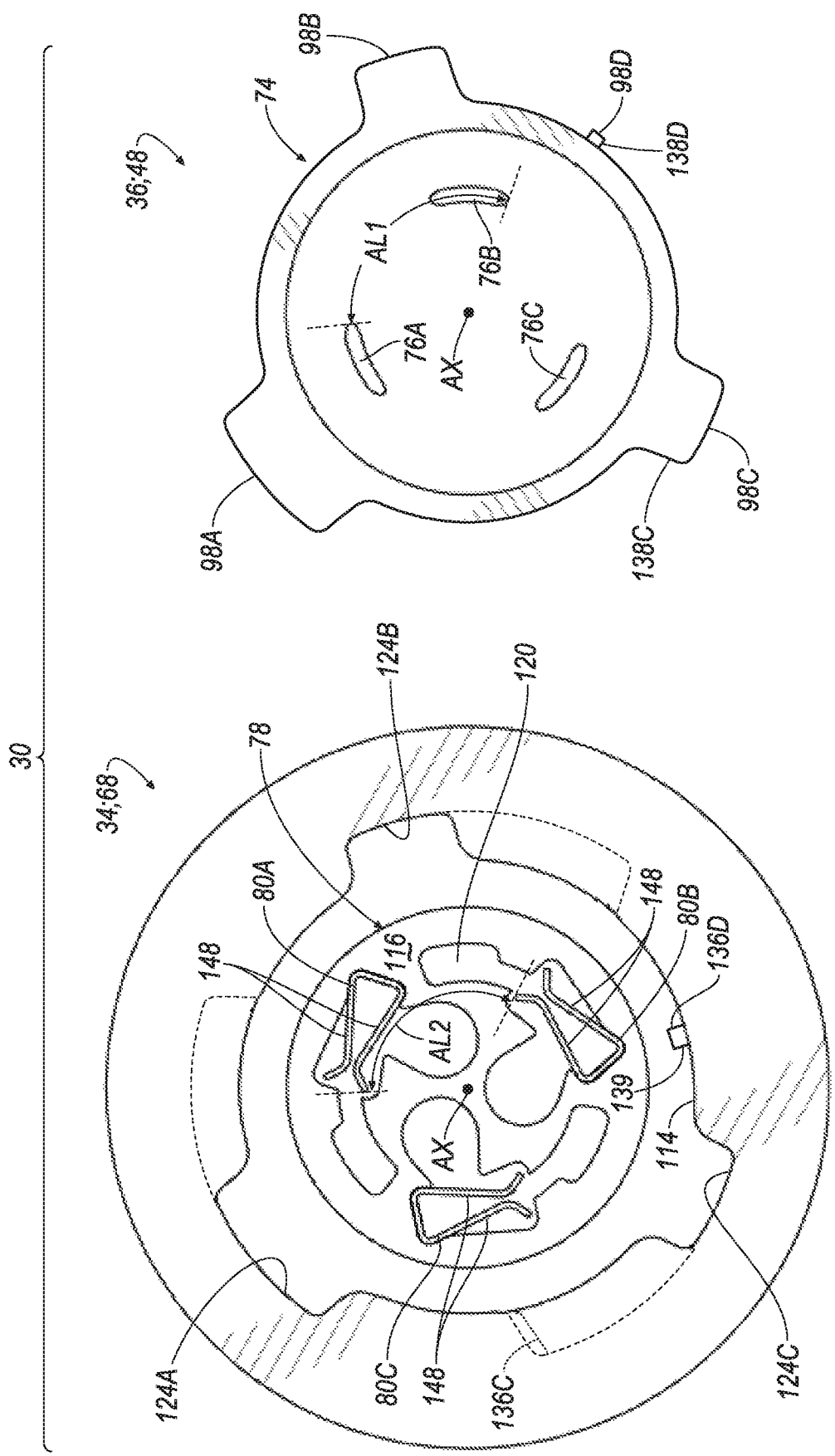
FIG. 13 is a schematic representation of the battery connector and the handpiece connector of FIGS. 12B-12E, positioned out of engagement and adjacent to each other.

Referring now to FIG. 13, in order to ensure that power and ground connections are established between the battery 34 and the handpiece 36 prior to data being communicated, in one example, the first handpiece terminal 76A and the second handpiece terminal 76B are radially spaced from each other about the axis AX at a handpiece terminal arc length AL1, and the first battery terminal 80A and the second battery terminal 80B are radially spaced from each other about the axis AX at a battery terminal arc length AL2 which is different from the handpiece terminal arc length AL1. In the example illustrated in FIG. 13, the battery terminals 80A, 80B, 80C are radially spaced from each other equidistantly about the axis AX, and the handpiece terminals 76A, 76B, 76C are radially spaced from each other non-equidistantly about the axis AX. This arrangement effects the difference between the handpiece terminal arc length AL1 and the battery terminal arc length AL2. However, those having ordinary skill in the art will appreciate that other arrangements of handpiece terminals 76A, 76B, 76C and/or battery terminals 80A, 80B, 80C could be employed.

Referring now to FIGS. 8-10, the first coupler 74 of the handpiece connector 48 may comprise a first coupler member 82, a terminal retainer 84, and one or more biasing elements 86. In the example illustrated in FIG. 10, the first coupler member 82 has a flange portion 88 and socket portion 90. The flange portion 88 has a flat, generally annular configuration, and is adapted to attach to the body 44 of the handpiece 36 as noted above. The socket portion 90 extends from the flange portion 88 to a first coupler end 92, and has a generally tapered-cylindrical profile defining an outer first coupler surface 94 and an inner first coupler surface 96, each of which are shaped to help guide the first coupler 74 into engagement with the second coupler 78. The handpiece terminals 76A, 76B, 76C are disposed within the socket portion 90 (see FIG. 9). The first coupler 74 also comprises a plurality of tabs 98A, 98B, 98C, 98D that may extend outwardly from the outer first coupler surface 94. A plurality of, e.g., three, alignment tabs 98A, 98B, 98C may be radially spaced from each other about the axis AX and help ensure proper alignment of the battery 34 and the handpiece 36 in the initial radial position IRP, as described in greater detail below. A stop tab 98D may be axially and radially positioned to limit relative rotative indexing of the battery 34 relative to the handpiece 36 to the SRPF position as will be described in greater detail below.

With continued reference to FIG. 10, the terminal retainer 84 supports the handpiece terminals 76A, 76B, 76C and is disposed between the first coupler member 82 and the body 44 of the handpiece 36. The terminal retainer 84 is provided with alignment keys 100 which are shaped to be disposed in correspondingly-shaped alignment pockets 102, 104 respectively formed in the first coupler member 82 and the body 44 of the handpiece 36 so as to ensure proper alignment of the handpiece terminals 76A, 76B, 76C with respect to the tabs 98A, 98B, 98C. The biasing elements 86 are similarly interposed between the first coupler member 82 and the body 44 of the handpiece 36, and are seated in separate bias apertures 106 defined in the flange portion 88 of the first coupler member 82. In the illustrated example, the biasing elements 86 each have a curved, generally rectangular profile and are configured to engage portions of the battery connector 68 to bias the handpiece connector 48 away from the battery connector 68 along the axis AX, which helps prevent inadvertent rotation from the secured radial positions SRP1, SRP2 and helps afford a consistent haptic feel during rotation between the battery 34 and the handpiece 36. The biasing elements 86 also help to dampen noise and/or vibration between the handpiece 36 and the battery 34 during use, which results in improved handling comfort and reduced component wear, such as may otherwise occur between one or more of the handpiece terminals 76A, 76B, 76C and/or the battery terminals 80A, 80B, 800C.

Referring now to FIGS. 4-7, in the example illustrated herein, the second coupler 78 of the battery connector 68 comprises a second coupler member 108 and a second coupler channel 110 formed adjacent to the second coupler member 108 (see FIG. 5). The second coupler member 108 defines a second coupler member surface 112 which is shaped to engage the inner first coupler surface 96 of the handpiece connector 48. The second coupler channel 110 defines an inner channel surface 114 which is shaped to engage the outer first coupler surface 94 of the handpiece connector 48. Thus, the socket portion 90 of the first coupler 74 of the handpiece connector 48 is shaped so as to be disposed within the second coupler channel 110 of the second coupler 78 of the battery connector 68. Here too, the second coupler member 108 has a tapered, generally cylindrical profile which is complimentarily-shaped to the socket portion 90 of the first coupler 74 so as to help guide the handpiece connector 48 into engagement with the battery connector 68. Other profiles are contemplated.

As is best depicted in FIG. 5, the second coupler member 108 of the second coupler 78 of the battery connector 68 extends to a second coupler end 116. A plurality of receptacles 118A, 118B, 118C are formed in the second coupler end 116 to accommodate the battery terminals 80A, 80B, 80C. More specifically, each of the receptacles 118A, 118B, 118C has an insertion portion 120 and an engagement portion 122. The battery terminals 80A, 80B, 80C are seated in the engagement portions 122 of the respective receptacles 118A, 118B, 118C and are spaced from the insertions portions 120 which, in turn, are shaped to axially receive the respective handpiece terminals 76A, 76B, 76C at the initial radial position (see FIG. 12B). The insertion portion 120 and the engagement portion 122 of each respective receptacle 118A, 118B, 18C are in communication with each other so as to facilitate movement of the handpiece terminals 76A, 76B, 76C from the initial radial position IRP (see FIG. 12B) to one or more of the plurality of secured radial positions SRP1, SRP2, SRPF (see FIGS. 12C-12E; see also FIGS. 14A-14C).

With continued reference to FIG. 5, the battery connector 68 comprises a plurality of slots 124A, 124B, 124C formed adjacent to the second coupler 78 to receive the respective tabs 98A, 98B, 98C of the handpiece connector 48 at the initial radial position IRP (see FIG. 12B), and to permit rotation of the battery 34 relative to the handpiece 36 between the initial radial position IRP and the plurality of secured radial positions SRP1, SRP2, SRPF. To this end, each of the slots 124A, 124B, 124C comprises an axial portion 126 to receive the respective tab 98A, 98B, 98C of the handpiece connector 48 at the initial radial position IRP, and a radial portion 128 adjacent to and in communication with the axial portion 126 to receive the respective tab 98A, 98B, 98C of the handpiece connector 48 in the plurality of secured radial positions SRP1, SRP2, SRPF.

Figure 12E:
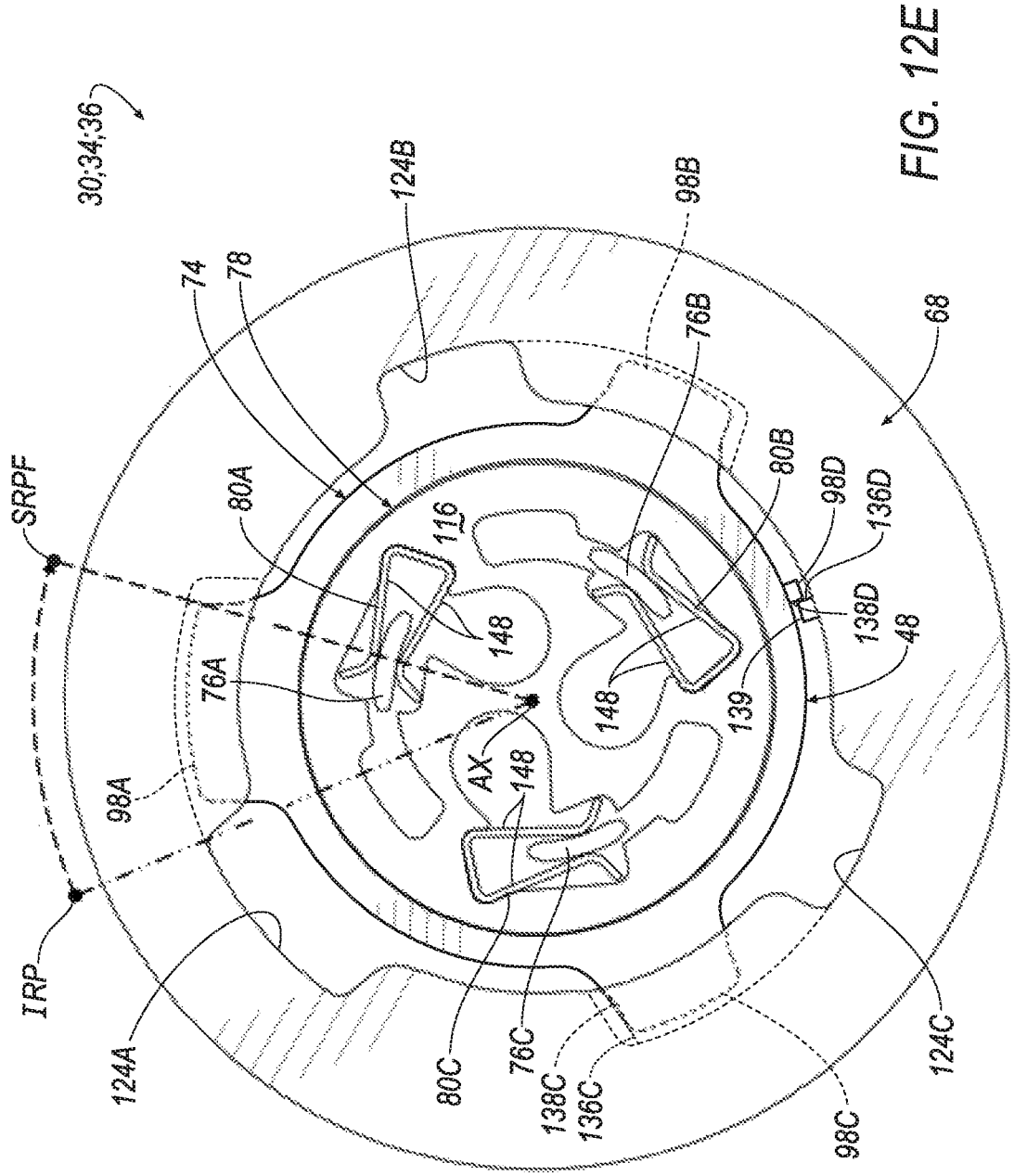
FIG. 12E is another schematic representation depicting engagement of the battery connector and the handpiece connector of FIG. 12D, shown with the handpiece connector rotated further to yet another secured radial position relative to the battery connector.

The radial portion 128 of each of the slots 124A, 124B, 124C defines a respective slot securing surface 130 which is shaped to engage against the respective tabs 98A, 98B, 98C in the secured radial positions SRP1, SRP2, SRPF to prevent relative axial movement between the battery 34 and the handpiece 36, as noted above. To this end, and as is best depicted in FIG. 9, each of the tabs 98A, 98B, 98C defines a tab securing surface 132 which is arranged to abut the slot securing surface 130 defined by each of the respective slots 124A, 124B, 124C when the tabs 98A, 98B, 98C are disposed in the radial portions 128 of the slots 124A, 124B, 124C (see also FIG. 12C; compare to FIG. 12B). In some examples, the tabs 98A, 98B, 98C of the handpiece connector 48 each comprise a transition chamfer 134 (see FIG. 9) which is shaped to facilitate movement from the initial radial position IRP (see FIG. 12B) toward one of the plurality of secured radial positions SRP1, SRP2, SRPF (see FIGS. 12C-12E). In one example, the radial portions 128 of one of the slots 124A, 124B, 124C, e.g., slot 124C, may define a respective slot stop surface 136C (shown in phantom in FIGS. 7 and 12A through 12E) which is shaped to abut a respective tab stop surface 138C (see FIGS. 12B through 12E) of a corresponding one of the tabs 98A, 98B, 98C, e.g., tab 98C, in the final secured radial position SRPF (see FIG. 12E). In such an example, the handpiece stop tab 98D and a battery stop tab 139, discussed below, are not needed. In an alternative arrangement in which contact between surfaces 136C and 138C is not needed, the battery stop tab 139 projects inwardly towards axis AX from the inner channel surface 114 and defines a battery stop surface 136D, and the handpiece stop tab 98D extends from the surface 94 outwardly away from the axis AX and defines a handpiece stop surface 138D. Both tabs 139 and 98D are illustrated as being substantially cubical in shape, but may have alternative shapes extending away from surfaces 136D and 138D (e.g., triangular, arcuate). Surfaces 136D and 138D may be coincident with planes extending away from and coincident with the axis AX. The handpiece stop tab 98D and the battery stop tab 139 are axially and radially positioned on their respective surface to align the handpiece stop surface 138D and the battery stop surface 136D. The handpiece stop surface 138D and the battery stop surface 136D engage against each other in the final secured radial position SRPF as illustrated in FIG. 12E. With this alternative example, the end of the radial portion 128 of slot 124C is beyond where surface 136C would otherwise be located, defining a gap between surface 138C and the end of slot 124C, as with be the corresponding surfaces of tabs 98A and 98B and the ends of slots 124A and 124B.

Referring now to FIGS. 2-13, as noted above, the tabs 98A, 98B, 98C cooperate with the slots 124A, 124B, 124C to help facilitate axial engagement between the handpiece connector 48 and the battery connector 68 along the axis AX in the initial radial position IRP. In the example illustrated throughout the drawings, the first tab 98A is shaped differently from the second and third tabs 98B, 98C, and the first slot 124A is likewise shaped differently from the second and third slots 124B, 124C, so as to prevent the first tab 98A of the handpiece connector 48 from being received within the second or third slots 124B, 124C of the battery connector 68. To this end, the second and third slots 124B, 124C are smaller than the first slot 124A (see FIG. 13). Thus, axial engagement between the handpiece 36 and the battery 34 along the axis AX is restricted to the initial radial position IRP, which is achieved when the first tab 98A is properly aligned to the first slot 124A (see FIG. 12B).

It will be appreciated that other arrangements and configurations of tabs 98A, 98B, 98C and/or slots 124A, 124B, 124C could be employed to prevent axial engagement from occurring outside of the initial radial position IRP. By way of non-limiting example, it is conceivable that each of the tabs 98A, 98B, 98C and slots 124A, 124B, 124C could be similarly sized, but could be radially spaced from each other in such a way as to prevent axial engagement from occurring outside of the initial radial position IRP, such as spaced non-equidistantly from each other. While three tabs 98A, 98B, 98C and three corresponding slots 124A, 124B, 124C are shown in the illustrative example, those having ordinary skill in the art will appreciate that different quantities of tabs and slots, of various configurations and arrangements suitable to facilitate axial engagement at the initial radial position IRP and to restrict relative axial movement in the secured radial positions SRP1, SRP2, SRPF, are contemplated.

It will be appreciated that the arrangement and configuration of the tabs 98A, 98B, 98C and the slots 124A, 124B, 124C prevents inadvertent contact from occurring between the handpiece terminals 76A, 76B, 76C and the battery terminals 80A, 80B, 80C as the battery 34 and the handpiece 36 are secured to each other, such as may be caused by improper alignment outside of the initial radial position IRP. As depicted in FIG. 5, in order to further prevent inadvertent contact, each of the battery terminals 80A, 80B, 80C extends axially to respective battery terminal end 140 which is spaced from the second coupler end 116 of the battery connector 68 at a battery terminal gap 142 defined between the battery terminal ends 140 and the second coupler end 116. Similarly, as depicted in FIG. 9, each of the handpiece terminals 76A, 76B, 76C extends axially to a respective handpiece terminal end 144 which is spaced from the first coupler end 92 of the handpiece connector 48 at a handpiece terminal gap 146 defined between the handpiece terminal ends 144 and the first coupler end 92. Because of the presence of the battery terminal gap 142 and the handpiece terminal gap 146, inadvertent contact occurring between the battery terminals 80A, 80B, 80C and the handpiece terminals 76A, 76B, 76C is prevented further.

Figure 14B:
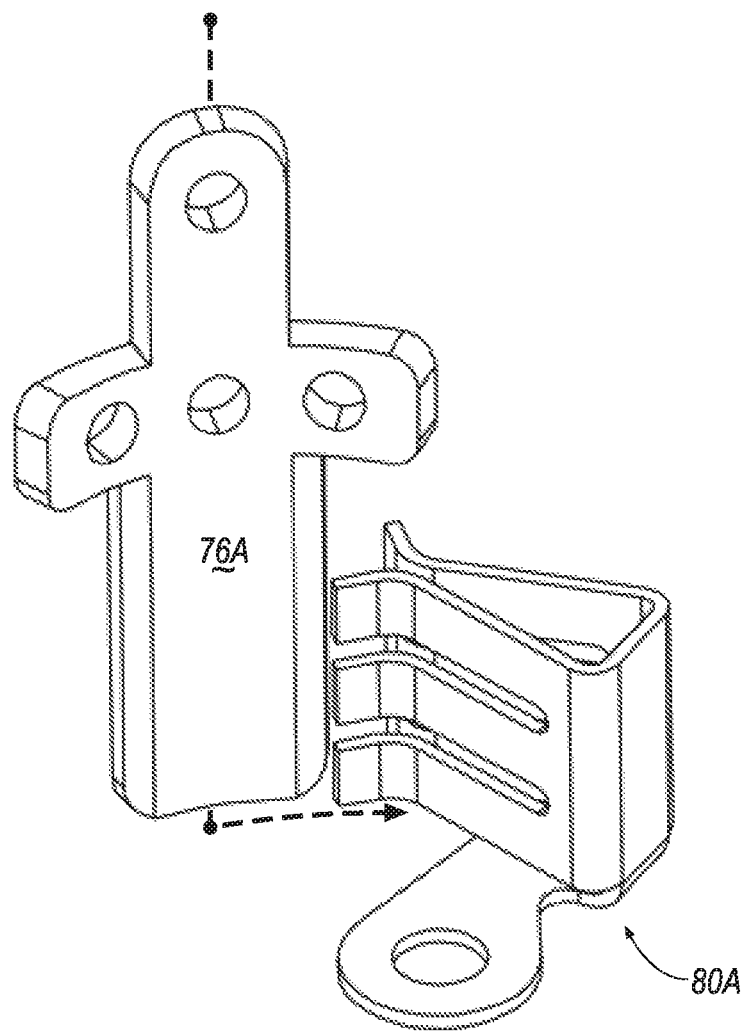
FIG. 14B is another perspective view of the handpiece terminal and the battery terminal of FIG. 14A, shown with the handpiece terminal arranged adjacent to the battery terminal.
Figure 14C:
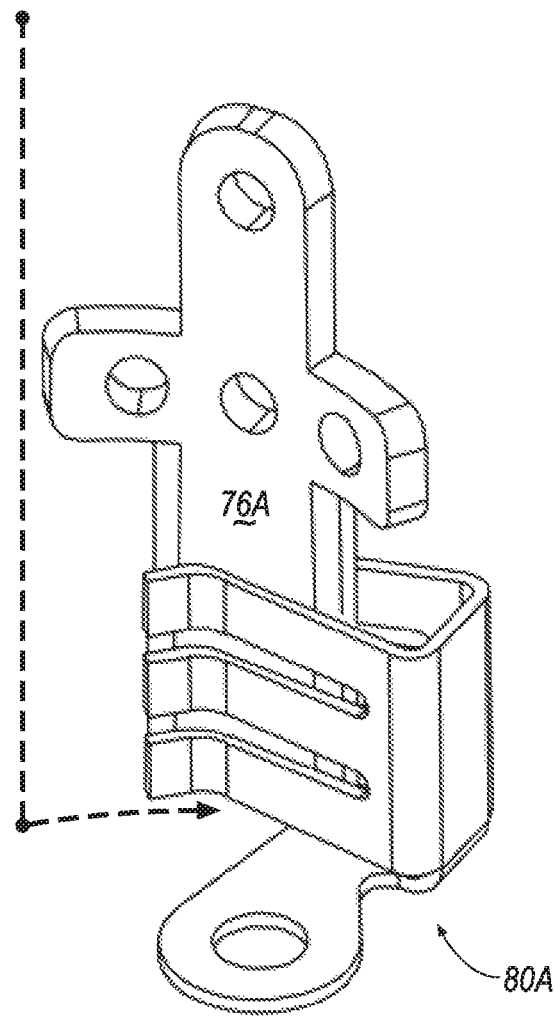
FIG. 14C is another perspective view of the handpiece terminal and the battery terminal of FIG. 14B, shown with the handpiece engaging the battery terminal.

Referring now to FIGS. 14A-14C, one of the handpiece terminals 76A and one of the battery terminals 80A are shown. In FIG. 14A, the handpiece terminal 76A is arranged in the manner depicted in FIG. 11B, spaced from the battery terminal 80A along the axis AX and arranged in the initial radial position IRP. FIG. 14B shows the handpiece terminal 76A arranged in the manner depicted in FIG. 11C, disposed adjacent to the battery terminal 80A along the axis AX and still arranged in the initial radial position IRP. While the second coupler 78 is omitted from view in FIGS. 14A-14C, it will be appreciated that the handpiece terminal 76A illustrated in FIG. 14B would be accommodated in the insertion portion 120 of one of the receptacles 118A, 118B, 118C in this arrangement. FIG. 14C shows the handpiece terminal 76A arranged in the manner depicted in FIG. 11E, engaged with the battery terminal 80A in the final secured radial position SRPF.

In the illustrated example depicted in FIGS. 14A-14C, each of the handpiece terminals 76A, 76B, 76C has a generally arc-shaped-rectangular profile, and each of the battery terminals 80A, 80B, 80C comprise a pair of arms 148 arranged to receive one of the handpiece terminals 76A, 76B, 76C therebetween. The arms 148 of each battery terminal 80A, 80B, 80C are resiliently biased towards each other to help facilitate repeated engagement and disengagement with the handpiece terminals 76A, 76B, 76C while, at the same time, ensuring that proper electrical contact is achieved when the battery 34 is secured to the handpiece 36. In the example, each of the arms 148 comprises a plurality of fingers 150 each arranged to engage one of the handpiece terminals 76A, 76B, 76C. Specifically, each arm 148 is provided with three fingers 150 which cooperate to engage the handpiece terminal 76A, 76B, 76C. Other arrangements are contemplated.

Referring now to FIGS. 4-15C, the surgical system 30 is provided with a lock, generally indicated at 152 in FIG. 11E, to prevent inadvertent rotation out of the final secured radial position FSRP. To this end, in one exemplary example, the handpiece connector 48 comprises a catch 154 arranged adjacent to the first coupler 74 (see FIGS. 8 and 9), and the battery 34 comprises a release mechanism 156 supported in the housing 62 (see FIGS. 6-7) and defining a latch 158 shaped to be received by and to engage the catch 154 in the final secured radial position SRPF to restrict subsequent rotation away from the final secured radial position SRPF. As illustrated in FIG. 9, the catch 154 is formed in the first coupler member 82 at the first coupler end 92, and has a generally rectangular profile arranged adjacent to the first tab 98A. The latch 158 of the release mechanism 156, as depicted in FIGS. 4-7, has a similar rectangular profile. The release mechanism 156 also defines a button, generally indicated at 160, which extends through a button aperture 162 that may be formed in an asymmetrical surface 163 of the first housing component 62A of the housing 62 and arranged for actuation by the surgeon or another user to facilitate disconnection of the battery 34 from the handpiece 36. The asymmetrical surface 163 is a generally superior surface, i.e., a generally upward-facing surface, that extends farther from the axis AX than other generally superior surfaces of the first housing component 62A. The asymmetrical surface 163 may extend distally forward relative to the hand grip 50. As used herein, "distally" indicates a direction away from the surgeon or other user of the system 30. A release bias element 164, e.g., a coil spring, may be interposed between the housing 62 and the release mechanism 156, and may be arranged to urge the latch 158 into engagement with the catch 154.

Figure 15A:
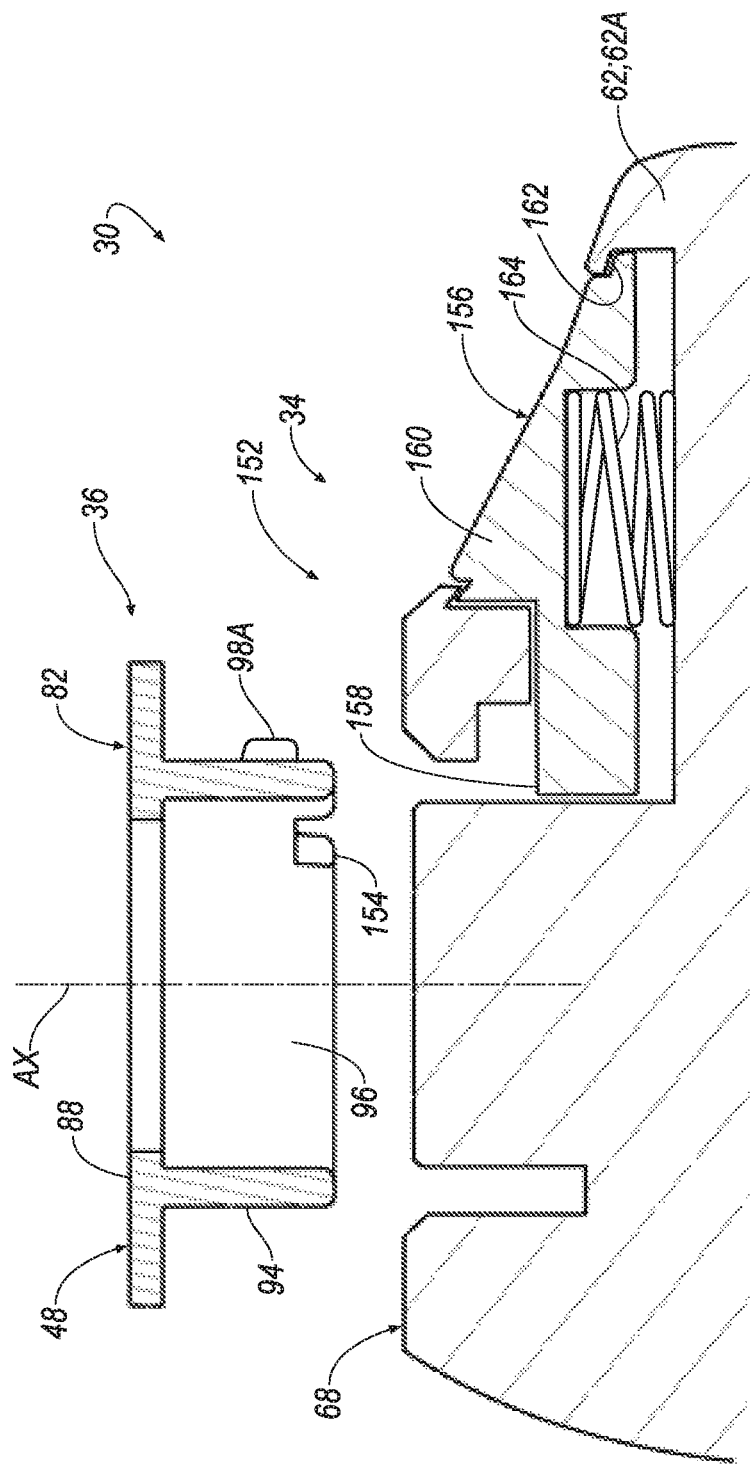
FIG. 15A is a schematic representation depicting a portion of the handpiece connector of FIG. 8 positioned adjacent to portions of the battery connector, the release mechanism, and the housing components of the battery of FIG. 6.
Figure 15B:
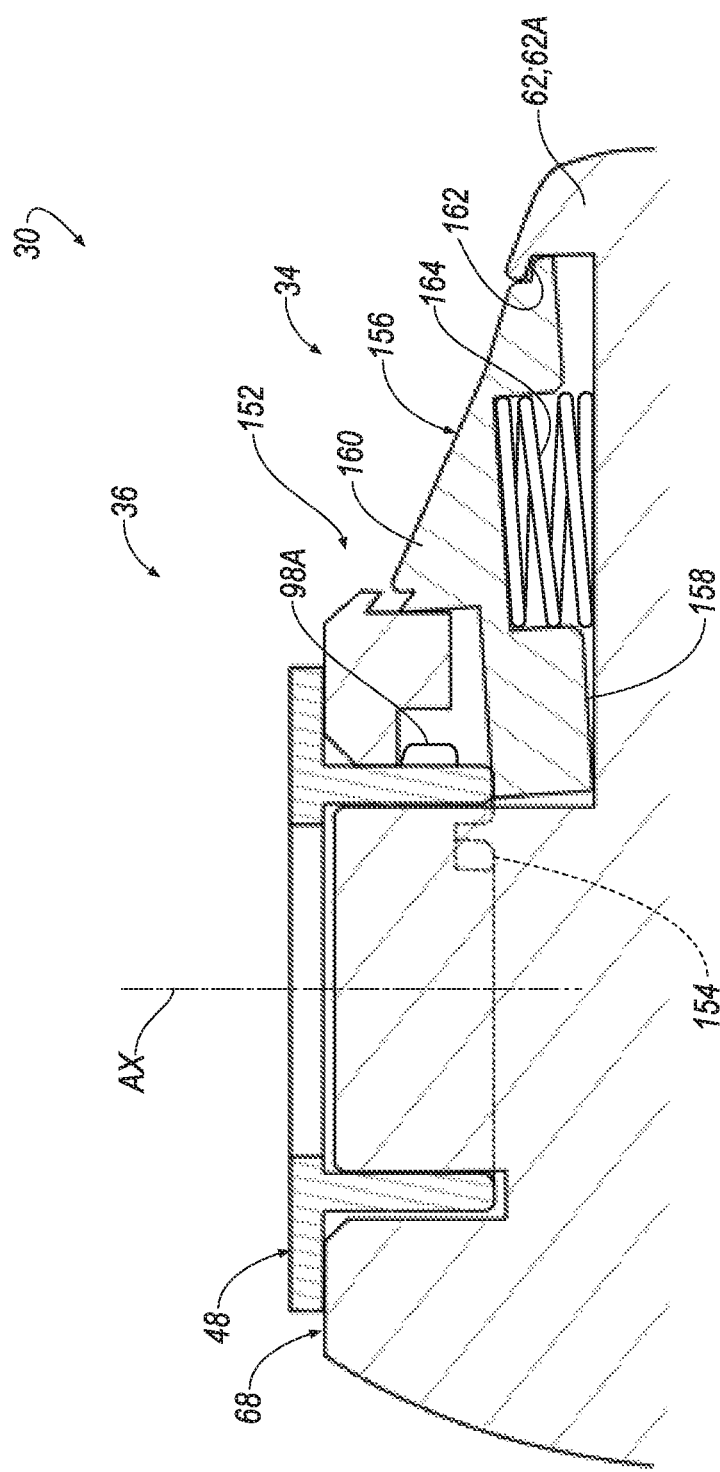
FIG. 15B is another schematic representation depicting the portions of the handpiece connector and the battery of FIG. 15A, shown with the handpiece connector abutting the release mechanism at the initial radial position depicted in FIG. 11C.
Figure 15C:
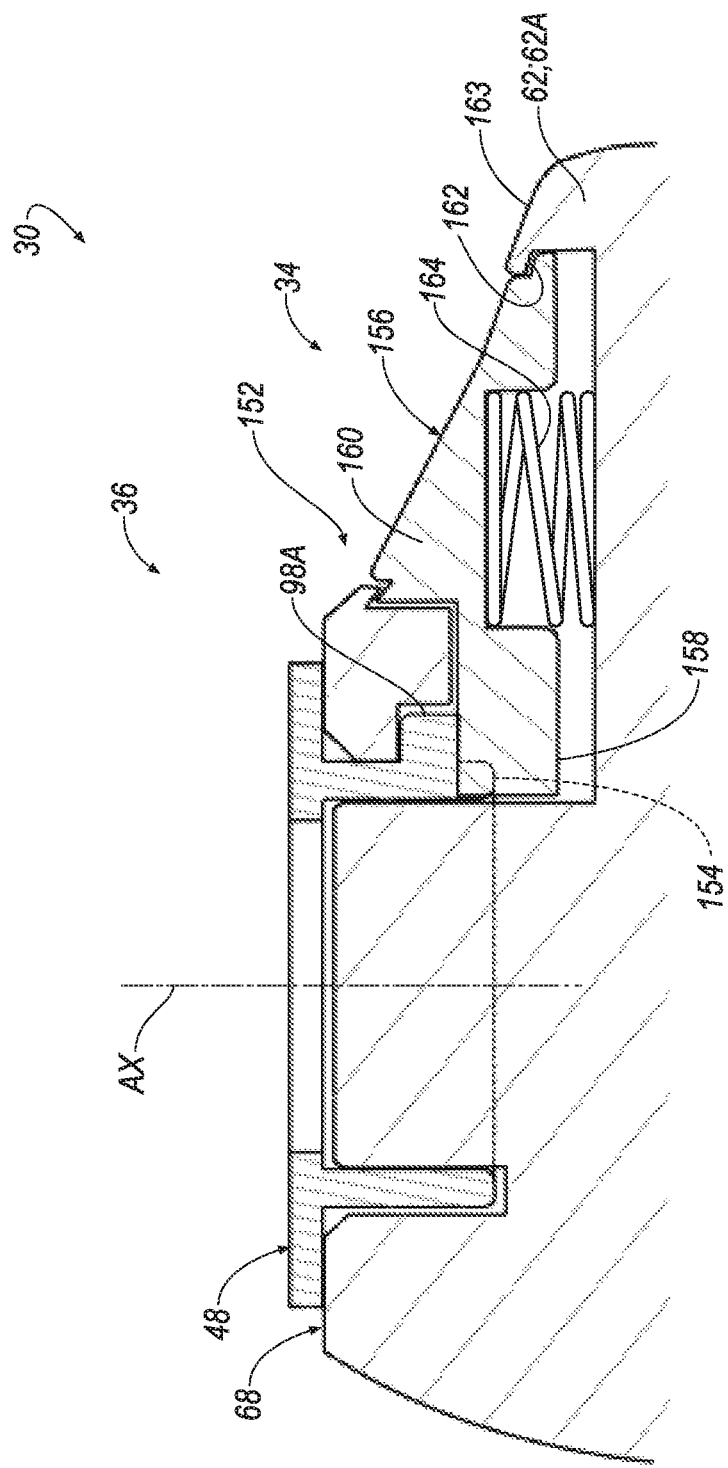
FIG. 15C is another schematic representation depicting the portions of the handpiece connector and the battery of FIG. 15B, shown with the release mechanism biased into engagement with the handpiece connector at the secured radial position depicted in FIG. 11E.

Referring now to FIGS. 15A-15C, schematic illustrative views of portions of the handpiece connector 48 and the battery connector 68 are shown to depict operation of the lock 152 sequentially. In FIG. 15A, the handpiece connector 48 is arranged in the manner depicted in FIG. 11B, spaced from the battery connector 68 along the axis AX and arranged in the initial radial position IRP. In FIG. 15B, the handpiece connector 48 is arranged in the manner depicted in FIG. 11C, disposed in engagement with the battery connector 68 along the axis AX and still arranged in the initial radial position IRP. Here in FIG. 15B, the first coupler end 92 of the first coupler 74 of the handpiece connector 48 is engaged against the latch 158 of the release mechanism 156 to compress the release bias element 164 (compare FIG. 15B with FIG. 15A) until subsequent rotation from the initial radial position IRP toward the final secured radial position SRPF brings the latch 158 and the catch 154 into engagement with each other, thereby "self-actuating" the lock 152 in response to rotation to the final secured radial position SRPF, as depicted in FIG. 15C (compare to FIG. 15B). Thus, rotation out of the final secured radial position SRPF is restricted until the button 160 is pressed to release the latch 158 from the catch 154.

A method of using the surgical system 30 described above is disclosed herein. The method comprises: providing the handpiece 36 comprising the handpiece connector 48 defining the axis AX; providing the autoclavable battery 34 comprising the battery connector 68 configured for releasable attachment to the handpiece connector 48; positioning the battery connector 68 along the axis AX; moving the battery connector 68 into axial engagement with the handpiece connector 48 at the initial radial position IRP; and rotating the battery 34 relative to the handpiece 36 about the axis AX from the initial radial position IRP to the secured radial position SRP1, SRP2, SRPF to secure the battery 34 to the handpiece 36. In one example, the method further comprises: rotating the battery 34 relative to the handpiece 36 about the axis AX from the secured radial position SRP1, SRP2, SRPF to the initial radial position IRP; and moving the battery connector 68 out of axial engagement with the handpiece connector 48 at the initial radial position IRP to remove the battery 34 from the handpiece 36. Other methods of using the surgical system 30 are also contemplated.

The surgical system 30 described herein affords significant advantages in connection with batteries 34 used to with surgical handpieces 36 and other modules 32, including chargers 38, instruments 40, and other tools used in connection with surgical and/or medical practices and procedures. Specifically, the configuration of the handpiece connector 48 and the battery connector 68 allows the battery 34 and the handpiece 36 to be releasably attached together in a simple, reliable, and efficient "twist-lock" manner. Moreover, the releasable attachment between the battery 34 and the handpiece 36 can be effected in a number of different conditions, such as where the surgeon or another user attempts to detach the battery 34 from the handpiece 36 while wearing sterile gloves, without necessitating the use of excessive force that might otherwise damage or deform components of the surgical system 30 which, in turn, could otherwise present safety and/or handling concerns.

Furthermore, it will be appreciated that the "twist-lock" connection afforded by the surgical system 30 described herein facilitates a consistent and reliable physical connection between the battery 34 and the handpiece 36 and, at the same time, ensures reliable electrical communication between the battery 34 and the handpiece 36 during use. Here, the configuration of the handpiece connector 48 and the battery connector 68 allows power and ground to be communicated between the battery 34 and the handpiece 36 prior to a data connection being established, which ensures that the handpiece controller 48 and the battery controller 66 can communicate, interact, and function properly during use. In addition, the handpiece connector 48 and the battery connector 68 cooperate to ensure that inadvertent contact between the handpiece terminals 76A, 76B, 76C and the battery terminals 80A, 80B, 80C is avoided.

It will be further appreciated that the terms "include," "includes," and "including" have the same meaning as the terms "comprise," "comprises," and "comprising." Moreover, it will be appreciated that terms such as "first," "second," "third," and the like are used herein to differentiate certain structural features and components for the non-limiting, illustrative purposes of clarity and consistency.

Several examples have been discussed in the foregoing description. However, the examples discussed herein are not intended to be exhaustive or limit the invention to any particular form. For example, one of the voltage terminals of each of the battery and the handpiece may be centered on axis AX with the data terminals and the other of the voltage terminals being spaced from axis AX as described above. The terminology which has been used is intended to be in the nature of words of description rather than of limitation. Many modifications and variations are possible in light of the above teachings and the invention may be practiced otherwise than as specifically described.

The invention claimed is:

1. A surgical system comprising:
  a handpiece comprising:
    a body,
    a handpiece controller, and
    a handpiece connector operatively coupled to the body and comprising a handpiece voltage terminal and a handpiece data terminal with each connected to the handpiece controller, and a first coupler; and an autoclavable battery comprising
- a housing,
- a rechargeable cell for storing an electric charge,
- a battery controller, and
- a battery connector operatively coupled to the housing and comprising a battery voltage terminal and a battery data terminal with each connected to the battery controller, and a second coupler configured to rotatably engage the first coupler;

wherein the second coupler is further configured to receive the first coupler along an axis at an initial radial position where relative axial movement between the battery and the handpiece is permitted, and to permit rotation of the battery relative to the handpiece from the initial radial position to a first secured radial position and a second secured radial position, wherein relative axial movement between the battery and the handpiece is constrained in the first secured radial position and in the second secured radial position; and wherein the handpiece terminals and the battery terminals are arranged such that rotation from the initial radial position to the first secured radial position brings the handpiece voltage terminal into engagement with the battery voltage terminal to transmit power between the cell and the handpiece controller, and rotation from the first secured radial position to the second secured radial position brings the handpiece data terminal into engagement with the battery data terminal to communicate data between the battery controller and the handpiece controller while maintaining engagement between the handpiece voltage terminal and the battery voltage terminal.

2. The surgical system as set forth in claim 1, wherein:
the handpiece voltage terminal and the handpiece data terminal are radially spaced from each other about the axis at a handpiece terminal arc length; and
the battery voltage terminal and the battery data terminal are radially spaced from each other about the axis at a battery terminal arc length different from the handpiece terminal arc length.

3. The surgical system as set forth in claim 1, wherein the handpiece connector further comprises a tab extending outwardly from the first coupler; and
wherein the battery connector further comprises a slot formed adjacent to the second coupler to receive the tab of the handpiece connector at the initial radial position and to permit rotation of the battery relative to the handpiece between the initial radial position and the first and second secured radial positions.

4. The surgical system as set forth in claim 3, wherein the slot of the battery connector comprises an axial portion to receive the tab of the handpiece connector at the initial radial position, and a radial portion adjacent to the axial portion to receive the tab in the plurality of secured radial positions.

5. The surgical system as set forth in claim 4, wherein the radial portion of the slot of the battery connector defines a slot securing surface; and
wherein the tab of the handpiece connector defines a tab securing surface arranged to abut the slot securing surface when the tab is disposed in the radial portion of the slot.

6. The surgical system as set forth in claim 5, wherein the tab of the handpiece connector comprises a transition chamfer shaped to facilitate movement from the initial radial position toward the first and second secured radial positions.

7. The surgical system as set forth in claim 1, wherein the handpiece connector further comprises a first tab extending outwardly from the first coupler; and a second tab spaced from the first tab extending outwardly from the first coupler; and
wherein the battery connector further comprises a first slot formed adjacent to the second coupler to receive the first tab of the handpiece connector at the initial radial position; and a second slot formed adjacent to the second coupler and spaced from the first slot to receive the second tab of the handpiece connector at the initial radial position.

8. The surgical system as set forth in claim 7, wherein the second slot of the battery connector is shaped differently from the first slot to prevent the first tab of the handpiece connector from being received within the second slot.

9. The surgical system as set forth in claim 7, wherein the second slot of the battery connector is smaller than the first slot to prevent the first tab of the handpiece connector from being received within the second slot.

10. The surgical system as set forth in claim 7, wherein the first coupler is further configured to be received by the second coupler along an axis; and
wherein the first and second tabs of the handpiece connector are radially spaced from each other about the axis to prevent the first tab of the handpiece connector from being received within the second slot of the battery connector.

11. The surgical system as set forth in claim 1, wherein the first coupler comprises an outer first coupler surface and an inner first coupler surface extending to a first coupler end.

12. The surgical system as set forth in claim 11, wherein the second coupler comprises:
a second coupler member defining a second coupler member surface shaped to engage the inner first coupler surface of the handpiece connector; and
a second coupler channel formed adjacent to the second coupler member and defining an inner channel surface shaped to engage the outer first coupler surface of the handpiece connector.

13. The surgical system as set forth in claim 12, wherein the second coupler member of the battery connector extends to a second coupler end; and
wherein a first receptacle is formed in the second coupler end to accommodate the battery voltage terminal, and a second receptacle is formed in the second coupler end to accommodate the battery data terminal.

14. The surgical system as set forth in claim 13, wherein the battery terminals each extend towards the second coupler end to respective battery terminal ends.

15. The surgical system as set forth in claim 14, wherein the battery terminal ends are spaced from the second coupler end.

16. The surgical system as set forth in claim 15, wherein a battery terminal gap is defined between the battery terminal ends and the second coupler end.

17. The surgical system as set forth in claim 11, wherein the inner first coupler surface of the handpiece connector defines a socket portion; and
wherein the handpiece terminals are disposed in the socket portion.

18. The surgical system as set forth in claim 11, wherein the handpiece terminals each extend towards the first coupler end to respective handpiece terminal ends.

19. The surgical system as set forth in claim 18, wherein the handpiece terminal ends are spaced from the first coupler end, defining a handpiece terminal gap therebetween.

20. The surgical system as set forth in claim 18, wherein a handpiece terminal gap is defined between the handpiece terminal ends and the first coupler end.

21. The surgical system as set forth in claim 1, wherein the handpiece terminals each have a generally arc-shaped-rectangular profile.

22. The surgical system as set forth in claim 1, wherein the battery terminals each comprise a pair of arms arranged to receive one of the handpiece terminals therebetween.

23. The surgical system as set forth in claim 22, wherein the arms of each of the battery terminals are resiliently biased towards each other.

24. The surgical system as set forth in claim 22, wherein the arms of each of the battery terminals comprise a plurality of fingers each arranged to engage one of the handpiece terminals.

25. The surgical system as set forth in claim 1,
wherein the handpiece connector further comprises a second handpiece voltage terminal;
wherein the battery connector further comprises a second battery voltage terminal; and
wherein the second handpiece voltage terminal and the second battery voltage terminal are arranged such that rotation from the initial radial position to the first secured radial position brings the second handpiece voltage terminal into engagement with the second battery voltage terminal.

26. The surgical system as set forth in claim 1, wherein handpiece connector further comprises a catch arranged adjacent to the first coupler; and
wherein the battery further comprises a release mechanism supported in the housing and defining a latch shaped to engage the catch in one of the secured radial positions to restrict rotation from the secured radial position.

27. The surgical system as set forth in claim 26, wherein the battery further comprises a release bias element interposed between the housing and the release mechanism arranged to urge the latch into engagement with the catch.

28. The surgical system as set forth in claim 27, wherein the first coupler is shaped to engage against the latch of the release mechanism at the initial radial position to compress the release bias element until rotation from the initial radial position toward one of the secured radial positions brings the latch and the catch into engagement.

29. The surgical system as set forth in claim 1, wherein the battery housing includes an asymmetrical surface.

30. The surgical system as set forth in claim 29, further comprising a release mechanism disposed at least in part in the battery housing and the release mechanism including a button disposed in the asymmetrical surface of the housing.

31. A surgical system comprising:
a module comprising:
a body,
a module controller, and
a module connector operatively coupled to the body and comprising a first coupler, a first module terminal, a second module terminal, and a third module terminal; and
an autoclavable battery comprising:
a housing,
a rechargeable cell for storing an electric charge,
a battery controller, and
a battery connector operatively coupled to the housing and comprising a second coupler to rotatably engage the first coupler, a first battery terminal, a second battery terminal, and a third battery terminal;
wherein the second coupler is further configured to receive the first coupler at an initial radial position where relative axial movement between the battery and the module is permitted, and to permit rotation of the battery relative to the module from the initial radial position to a first secured radial position and a second secured radial position, wherein relative axial movement between the battery and the module is constrained in the first secured radial position and in the second secured radial position; and
wherein the module terminals and the battery terminals are arranged such that rotation from the initial radial position to the first secured radial position brings the first module terminal into engagement with the first battery terminal, and rotation from the first secured radial position to the second secured radial position brings the second module terminal into engagement with the second battery terminal while maintaining engagement between the first module terminal and the first battery terminal.

32. The surgical system as set forth in claim 31, wherein the module is further defined as a handpiece for performing a surgical procedure.

33. The surgical system as set forth in claim 31, wherein the module is further defined as a charger for the rechargeable cell.

34. The surgical system as set forth in claim 31,
wherein the module terminals and the battery terminals are arranged such that rotation from the initial radial position to the first secured radial position brings the third module terminal into engagement with the third battery terminal, and rotation from the first secured radial position to the second secured radial position maintains engagement between the third module terminal and the third battery terminal.

* * * * *